(12) United States Patent
Pfahl et al.

(10) Patent No.: US 6,462,064 B1
(45) Date of Patent: *Oct. 8, 2002

(54) APOPTOSIS INDUCING ADAMANTYL DERIVATIVES AND THEIR USAGE AS ANTI-CANCER AGENTS, ESPECIALLY FOR CERVICAL CANCERS AND DYSPLASIAS

(75) Inventors: Magnus Pfahl, Solana Beach; Xian-Ping Lu; Darryl Rideout, both of San Diego; Hongyue Zhang, La Jolla, all of CA (US)

(73) Assignee: Galderma Research & Development S.N.C., Valbonne (FR)

( * ) Notice: Subject to any disclaimer, the term of this patent is extended or adjusted under 35 U.S.C. 154(b) by 0 days.

This patent is subject to a terminal disclaimer.

(21) Appl. No.: 09/498,347

(22) Filed: Feb. 4, 2000

Related U.S. Application Data

(63) Continuation-in-part of application No. 09/214,422, filed as application No. PCT/US97/11564 on Jul. 8, 1997, now Pat. No. 6,127,415.
(60) Provisional application No. 60/021,285, filed on Jul. 8, 1996.

(51) Int. Cl.[7] .................. A61K 31/415; A61K 31/235; A61K 31/385; A61K 31/35; A61K 31/335; A61K 31/19
(52) U.S. Cl. .................. 514/394; 514/543; 514/435; 514/437; 514/454; 514/455; 514/452; 514/569
(58) Field of Search .................. 514/543, 435, 514/437, 454, 455, 452, 569, 394

(56) References Cited

U.S. PATENT DOCUMENTS

| | | |
|---|---|---|
| 4,347,254 A | 8/1982 | Katsube et al. |
| 4,391,819 A | 7/1983 | Thies et al. |
| 5,098,929 A | 3/1992 | Larkin et al. |
| 5,547,983 A | 8/1996 | Charpentier et al. |
| 5,770,382 A | 6/1998 | Hwang et al. |
| 5,877,342 A | 3/1999 | Bernardon et al. |
| 5,888,432 A | 3/1999 | Chan |
| 5,919,970 A | 7/1999 | Song et al. |
| 6,127,415 A | * 10/2000 | Pfahl .................. 514/543 |

FOREIGN PATENT DOCUMENTS

| | | |
|---|---|---|
| WO | 97/03682 A1 | 2/1997 |

OTHER PUBLICATIONS

Shao Z-M et al, "P53 Independent G0/G1 Arrest and Apoptosis Induced by a Novel Retinoid in Human Breast Cancer Cells," Oncogene, GB, Basingstoke, Hants, vol. 11, No. 3, Aug. 3, 1995, pp. 493–504, XP000575582.

Schadendorf D et al, "Retinoic Acid Receptor–Gamma–Selective Retinoids Exert Antiproliferative Effects on Human Melanoma Cell Growth In Vitro," Int'l J. Oncology, GR, Ed. Academy Int'l J. Oncology, vol. 5, No. 6, Dec. 1, 1994, pp. 1325–1331, XP000600684.

Charpentier B et al, "Synthesis, Structure–Affinity Relationships, and Biological Activities of Ligands Binding to Retinoic Acid Receptor Subtypes," J. Medicinal Chem., US, ACS, Washington, vol. 38, No. 26, Dec. 22, 1995, pp. 4993–5006, XP002026831.

European Search Report, appl. No. EP 97 93 3256, 2 pages.

* cited by examiner

*Primary Examiner*—Jerome D. Goldberg
(74) *Attorney, Agent, or Firm*—Burns, Doane, Swecker & Mathis, L.L.P.

(57) ABSTRACT

The invention relates to the discovery that specific adamantyl or adamantyl group derivatives containing retinoid-related compounds induce apoptosis of cancer cells and therefore may be used for the treatment of cancer, including advanced cancer. Also, the present invention relates to novel adamantyl or adamantyl group derivatives containing retinoid compounds and their usage for treatment and/or prevention of cancer, keratinization disorders, dermatological conditions, and other therapies More specifically, it has been shown that such adamantyl compounds, e.g., 6-[3-(1-adamantyl)-4-methoxyphenyl]-2-naphthoic acid, 2-[3-(1-adamantyl)-4-methoxyphenyl]-5-benzimidazole carboxylic acid, and 6-[3-(1-adamantyl)-4,5-methylenedioxyphenyl]-2-naphthoic acid, can be used to treat or prevent cervical cancers and precancers such as cervical dysplasias, including high grade and low grade dysplasias.

42 Claims, 11 Drawing Sheets

Experimental Data Output for Lead Identification

| Chemical Name | Bre | Cor | Col | Fib | Gli | HN | Lu | Mel | Neu | Ov | Pan | Pro |
|---|---|---|---|---|---|---|---|---|---|---|---|---|
| all-*trans*-retinoic acid | 97 | 91 | 124 | 114 | 91 | 79 | 82 | 111 | 122 | 103 | 94 | 115 |
| 6 (3 (1 adamantyl) 4 methoxyphenyl) 2 naphthoic acid | 6 | 79 | 103 | 105 | 81 | 70 | 63 | 87 | 43 | 107 | 84 | 77 |
| 2 (3 (1 adamantyl) 4 methoxyphenyl) 5 benzimidazole carboxylic acid | 9 | 61 | 104 | 103 | 97 | 39 | 48 | 80 | 88 | 104 | 52 | 48 |
| 6 (3 (1 adamantyl) 4 hydroxymethylphenyl) 2 naphthoic acid | 4 | 70 | 1 | 31 | 69 | 10 | 30 | 43 | 26 | 4 | 40 | 12 |
| 6 (3 (1 adamantyl) 4 hydroxy 5 methoxyphenyl) 2 naphthoic acid | 33 | 81 | 103 | 76 | 41 | 23 | 42 | 68 | 64 | 81 | 56 | 26 |
| 6 (3 (1 adamantyl) 4 acetoxymethylphenyl) 2 naphthoic acid | 81 | 92 | 103 | 87 | 83 | 83 | 77 | 101 | 115 | 85 | 101 | 49 |
| 6 (3 (1 adamantyl) 4,5 methylenedioxyphenyl) 2 naphthoic acid | 31 | 95 | 99 | 74 | 87 | 25 | 36 | 17 | 6 | 56 | 68 | 100 |

FIG. 1

APOPTOSIS INDUCING ADAMANTYL DERIVATIVES AND THEIR USAGE AS ANTI-CANCER AGENTS, ESPECIALLY FOR CERVICAL CANCERS AND DYSPLASIAS

CROSS-REFERENCE TO RELATED APPLICATIONS

This application is a continuation-in-part of U.S. application Ser. No. 09/214,422, filed Apr. 14, 1999, now U.S. Pat. No. 6,127,415 which claims priority under §371 to PCT/US97/11564, filed Jul. 8, 1997, which in turn claims priority to U.S. Provisional Application No. 60/021,285, filed Jul. 8, 1996. All of these applications are incorporated by reference in their entirety herein.

TECHNICAL FIELD OF THE INVENTION

The invention relates to the discovery that specific adamantyl or adamantyl group derivative containing retinoid related compounds induce apoptosis of cancer cells and therefore may be used for the treatment or prevention of cancer, including advanced cancers and precancers. Also, the present invention relates to novel adamantyl or adamantyl group derivative containing retinoid related compounds and their use for the treatment and/or prevention of cancer, keratinization disorders, dermatological conditions and other therapies. A preferred application of the subject compounds is for the treatment or prevention of cervical cancers and precancers.

BACKGROUND OF THE INVENTION

Solid tumors are the leading cause of death attributable to cancers worldwide. Conventional methods of treating cancer include surgical treatments, the administration of chemotherapeutic agents, and recently immune based treatments which typically involve the administration of an antibody or antibody fragment which may be conjugated to a therapeutic moiety such as a radionuclide. However, to date, such treatments have been of limited success.

Surgical treatments are generally only successful if the cancer is detected at an early stage, i.e., before the cancer has infiltrated major organs and surgery becomes non-feasible. Chemotherapeutic treatments available today are also of limited usefulness because of their non-selective killing and/or toxicity to most cell types. Also, many tumor cells eventually become resistant against the chemotherapeutic agent, thus making treatment of solid tumors and other tumors non-feasible. For example, persons treated with cisplatin often develop tumors which are cisplatin resistant. Immune based treatments are also subject to numerous problems including difficulty in targeting antibodies to desired sites, e.g., solid tumors, and host immune reactions to the administered antibody, attributable to the fact that to date most therapeutic antibodies have been of murine origin.

The usage of retinoids for the prevention of cancer has also been reported. In contrast to most conventional chemotherapeutic agents, retinoids function via specific signal transduction pathways, activating defined receptors in the cell nucleus. These receptors, the RARs, and the RXRs bind to specific DNA sequences, retinoic acid response elements, or RAREs. In addition, retinoids interact with other transcription factors, in particular the activator protein-1 (AP-1).

It is believed that the selective action of certain synthetic retinoids is based on the ability of these molecules to selectively activate subclasses of RARs and/or RXRs in the context of specific DNA sequences and/or proteins. Because of this specificity, not all retinoids possess the same activities. Indeed, thousands of different retinoids have been synthesized with the object being the identification of retinoids having optimal therapeutic activity.

To date, most retinoids have been found to inhibit tumor progression or cell proliferation of certain cancers, but do not directly eliminate cancer cells. Consequently, retinoids have been considered predominantly for the prevention of cancer but not for direct treatment.

One special class of retinoids or retinoid related compounds comprises adamantyl retinoid derivatives. These compounds are aromatic heterocyclic retinoids which contain an adamantyl group or an adamantyl group derivative. In contrast to normal retinoids such as retinoic acid (all-trans, 9-cis or 13-cis) and their synthetic analogs and derivatives, the adamantyl retinoid derivatives exhibit enhanced activity against specific tumor cells both in vitro and in vivo.

Retinoids also comprise known usage in the treatment of keratinization disorders and other dermatological diseases. For example, the use of retinoic acid, vitamin D or analogues thereof for the topical treatment of various dermatological diseases and in the cosmetic field is well known.

However, notwithstanding the large number of retinoids which have been reported, the identification of retinoids or retinoid related compounds having enhanced properties, in particular enhanced therapeutic activity, constitutes a significant need in the art.

BRIEF DESCRIPTION AND OBJECTS OF THE INVENTION

It is an object of the invention to identify specific retinoid or retinoid related compounds having enhanced properties, in particular anti-cancer activity.

It is a more specific object of the invention to identify specific classes of adamantyl or adamantyl derivative containing retinoid related compounds having anti-cancer activity, preferably characterized by the ability to induce apoptosis of cancer cells.

It is an even more specific object of the invention to use adamantyl retinoid related compounds of the following formulae for the treatment of cancer:

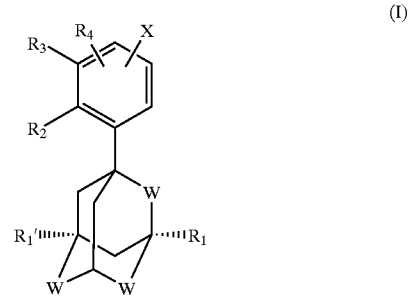

(I)

with the proviso that such compound is not an RAR-γ receptor-specific agonist ligand (defined infra) and, in which W is independently —CH$_2$—, —O—, —S—, —SO— or —SO$_2$—, X is a radical selected from among those of the following formulae (i)–(iii):

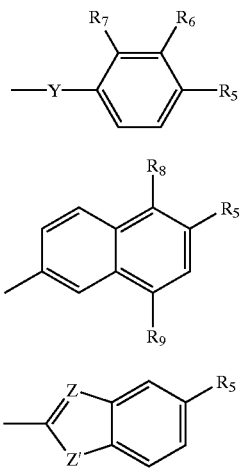

(i)

(ii)

(iii)

wherein
Y is a radical —CO—V—, —CH=CH—, —CH₃C=CH—, —CH=CCH₃—,

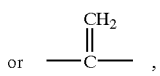

or

—CHOH—CH₂—,

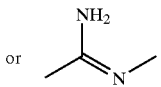

or

V is an oxygen atom (—O—), an aza radical (—NH—), a radical —CH=CH— or —C≡C—;

Z is a radical —CH— and Z' is an oxygen atom, or Z is a nitrogen atom (N) and Z' is an aza radical (—NH—);

$R_1$ is a hydrogen atom, a halogen, or a lower alkyl radical;

$R'_1$ is a hydrogen atom, a halogen, or a lower alkyl radical;

$R_2$ is a hydroxyl radical, a halogen, an alkyl radical, optionally substituted by one or more hydroxyl or acyl groups, an alkoxyl radical, optionally substituted by one or more hydroxyl, alkoxyl or aminocarbonyl groups, and/or optionally interrupted by one or more oxygen atoms, an acyl radical, an aminocarbonyl radical or a halogen;

$R_3$ is a hydrogen atom, a halogen, an hydroxyl radical, an alkyl radical, or an alkoxyl radical;

$R_2$ and $R_3$ can form together a radical —O—CH₂—O—;

$R_4$ is a hydrogen atom, an alkyl radical, an alkoxyl radical or a halogen;

$R_5$ is a radical —CO—$R_{10}$, an alkyl radical, optionally substituted by one or more hydroxyl groups, or a halogen;

$R_6$ is a hydrogen atom, a halogen atom, an alkoxyl radical, or hydroxyl group;

$R_7$ is a hydrogen atom or a halogen;

$R_8$ is a hydrogen atom, a halogen atom or an alkyl radical;

$R_9$ is a hydrogen atom, a hydroxyl radical or a halogen atom;

$R_{10}$ is a hydroxyl radical, an alkoxy radical, a radical of formula —Nr'r'', wherein r' and r'' represent a hydrogen atom, an optionally substituted aminoalkyl radical, a mono- or polyhydroxyalkyl radical, an optionally substituted aryl radical or an amino acid or sugar residue or alternatively, taken together, form a heterocycle;

or a compound having generic formula (III):

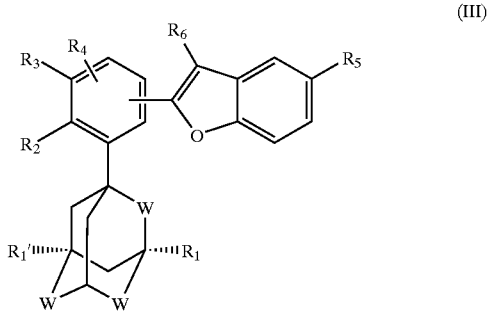

(III)

wherein $R'_1$, $R_1$, $R_2$, $R_3$, $R_4$, $R_5$, $R_6$ and W are as defined for compounds of formula (I); or a compound having generic formula:

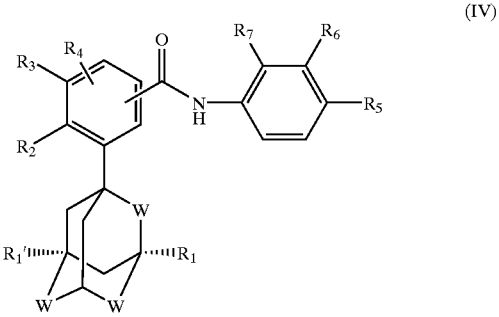

(IV)

wherein $R'_1$, $R_1$, $R_2$, $R_3$, $R_4$, $R_5$, $R_6$, $R_7$ and W are as defined for compounds of formula (I). For compounds having formula IV, $R_6$ is preferably not hydrogen.

It is a further object of the invention to provide novel classes of adamantyl and adamantyl derivative containing retinoids having desirable pharmacological and/or cosmetic properties.

It is a more specific object of the invention to provide novel classes of adamantyl and adamantyl derivative containing retinoids having desirable pharmacological and/or cosmetic properties having the formula set forth below:

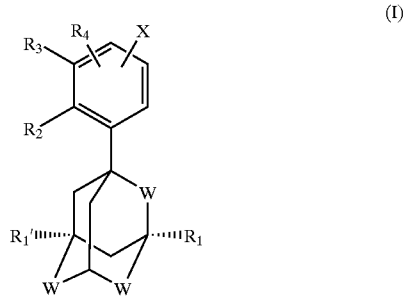

(I)

wherein
W is independently —CH₂—, —O—, —S—, —SO— or —SO₂—,

X is a radical selected from among those of the following formulae (i)–(iii)

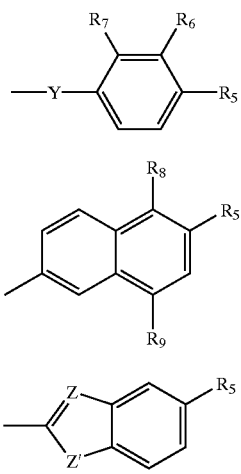

wherein
Y is a radical —CO—V—, —CH=CH—, —CH₃=CH—, —CH=CCH₃—,

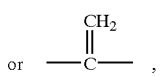

or

—CHOH—CH₂—O—,

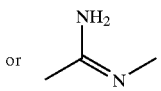

or

V is an oxygen atom (—O—), an aza radical (—NH—), a radical —CH=CH— or —C≡C—;
Z is a radical —CH— and Z' is an oxygen atom, or
Z is a nitrogen atom (N) and Z' is an aza radical (—NH—);
$R_1$ is a hydrogen atom, a halogen, or a lower alkyl radical;
$R'_1$ is a hydrogen atom, a halogen, or a lower alkyl radical;
$R_2$ is a hydroxyl radical, a halogen atom, an alkyl radical, optionally substituted by one or more hydroxyl or acyl groups, an alkoxyl radical, optionally substituted by one or more hydroxyl, alkoxyl or aminocarbonyl groups, and/or optionally interrupted by one or more oxygen atoms, an acyl radical, an aminocarbonyl radical or a halogen;
$R_3$ is a hydrogen atom, a halogen, an hydroxyl radical, an alkyl radical, or an alkoxyl radical;
$R_2$ and $R_3$ can form together a radical —O—CH₂—O—;
$R_4$ is a hydrogen atom, an alkyl radical, an alkoxyl radical or a halogen;
$R_5$ is a radical —CO—$R_{10}$, an alkyl radical, optionally substituted by one or more hydroxyl groups, or a halogen;
$R_6$ is a hydrogen atom, a halogen atom or an alkoxyl radical, or hydroxyl group;
$R_7$ is a hydrogen atom or a halogen;
$R_8$ is a hydrogen atom, a halogen atom or an alkyl radical;
$R_9$ is a hydrogen atom, a hydroxyl radical or a halogen atom;
$R_{10}$ is a hydroxyl radical, an alkoxy radical, a radical of formula —Nr'r", wherein r' and r" represent a hydrogen atom, an optionally substituted aminoalkyl radical, a mono- or polyhydroxyalkyl radical, an optionally substituted aryl radical, or an amino acid or sugar residue, or alternatively, taken together, form a heterocycle, their pharmaceutically acceptable salts, their optical and/or geometrical isomers thereof;

with the proviso that at least two of $R_2$, $R_3$ and $R_4$ cannot be hydrogen and the further proviso that $R_2$ and $R_3$ cannot together form —O—CH₂—O—, or is a compound of general formula (I);

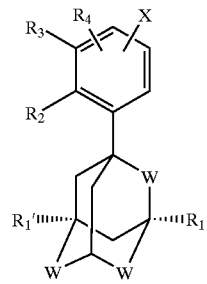

wherein V, W, $R_1'$, $R_1$, $R_2$, $R_3$, $R_4$, $R_5$, $R_6$, $R_7$, $R_8$, $R_9$, $R_{10}$, X, Y, Z', Z are as defined supra, with the proviso that at least one of W is —O—, —S—, —SO—, or —SO₂—, and/or at least one of $R_1$ and $R_1'$ is halogen or a lower alkyl radical, and more preferably at least one W is —O— and/or $R_1$ is a lower alkyl radical and/or $R_1'$ is a lower alkyl radical;

or is a compound of generic formula (I);

wherein V, W, $R_1'$, $R_1$, $R_2$, $R_3$, $R_4$, $R_5$, $R_6$, $R_7$, $R_8$, $R_9$, $R_{10}$, Y, Z and Z' are as defined supra, with the proviso that $R_5$ is —CO—$R_{10}$ and $R_{10}$ is a radical of formula —Nr'r", wherein one of r' and r" is hydrogen, and the other is an optionally substituted aminoalkyl radical or alternatively r' and r", together, form a heterocycle, preferably a piperazino or a homolog thereof; where preferably X has formula (ii) and/or $R_8$ is preferably hydrogen and/or $R_9$ is preferably hydrogen.

or is a compound of formula (III):

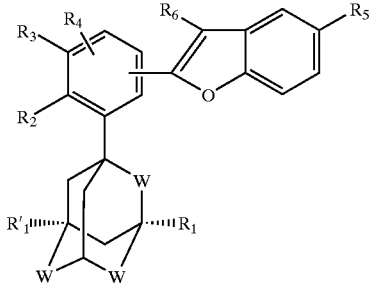

wherein $R'_1$, $R_1$, $R_2$, $R_3$, $R_4$, $R_5$, $R_6$ and W are as defined for compounds of formula (I).

It is another object of the invention to provide therapeutic and/or cosmetic compositions containing such novel retinoid compounds.

It is a further object of the invention to provide therapeutic/prophylactic/cosmetic methods involving the administration of a novel adamantyl or adamantyl derivative compound according to the invention. Such methods will include known usages of retinoid compounds, in particular, usage for treatment/prophylaxis of keratolytic associated disorders associated with differentiation and/or proliferation and other dermal related disorders.

BRIEF DESCRIPTION OF THE FIGURES

FIG. 1 compares the activity of selected adamantyl retinoids according to the invention and all-trans-retinoic acid against human cancer cell lines.

DETAILED DESCRIPTION OF THE INVENTION

Figure 2:
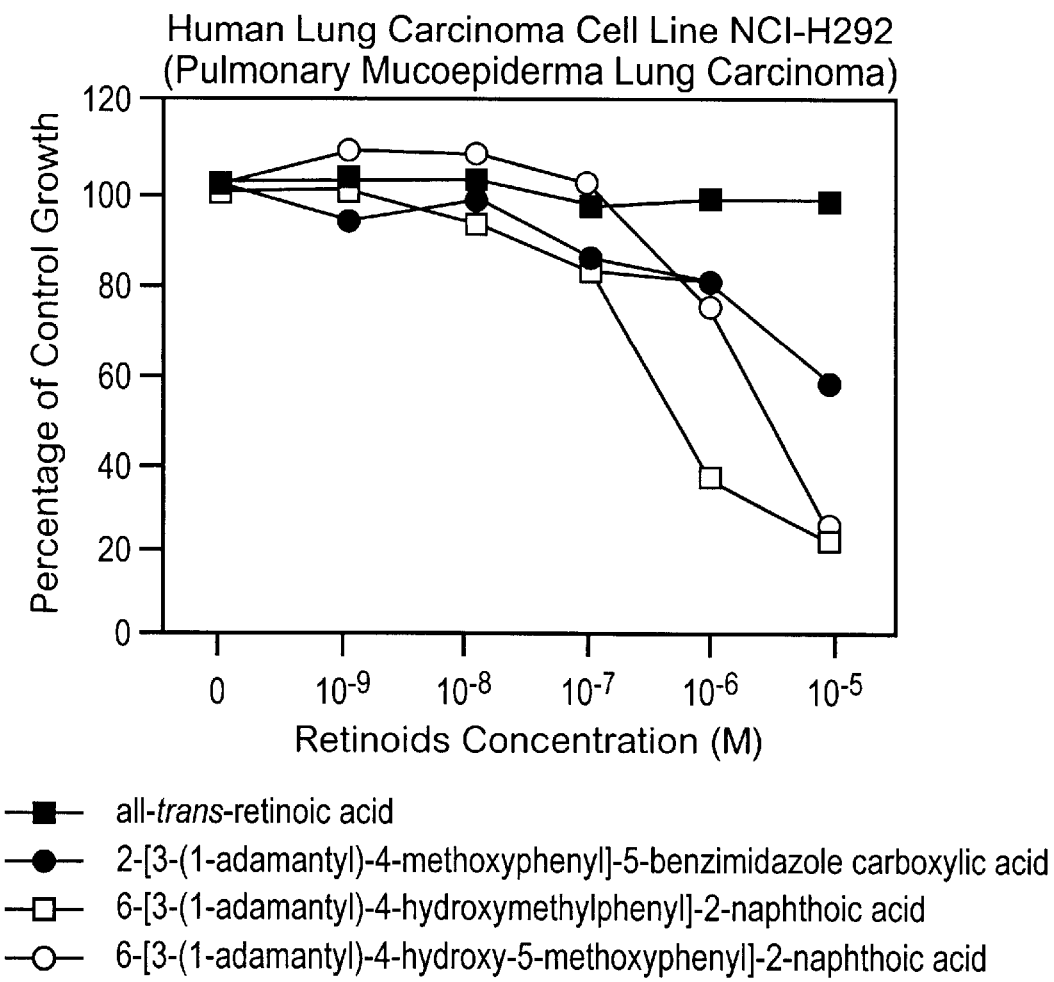
FIG. 2 compares the activity of selected adamantyl retinoids according to the invention and all-trans-retinoic acid against a human non-small lung carcinoma cell line.

Toward that end, the present inventors, quite surprisingly, have discovered that specific adamantyl retinoid derivatives induce apoptosis of cancer cells. This is highly unexpected as in contrast to most conventional chemotherapeutic agents, retinoids and also most known adamantyl retinoids, function via specific signal transduction pathways, activating defined receptors in the cell nucleus. By contrast, it has been unexpectedly discovered that the specific adamantyl retinoid derivatives which are disclosed infra induce cancer cell apoptosis and therefore may be used to eradicate cancer cells. Consequently, these retinoids may be used for the direct treatment of cancers, including advanced cancers. In particular, these retinoids may be used to treat or prevent cervical dysplasias and cancers, both in very early and advanced stages.

More specifically, the present invention relates to the use of adamantyl retinoid derivatives having the following formula (I) for inducing apoptosis:

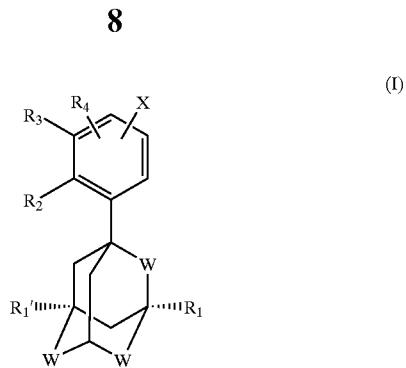

wherein
W is independently —$CH_2$—, —O—, —S—, —SO— or —$SO_2$—,
X is a radical selected from among those of the following formulae (i)–(iii)

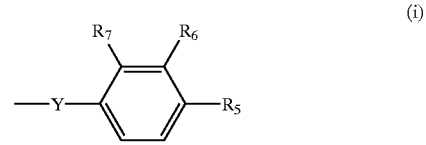

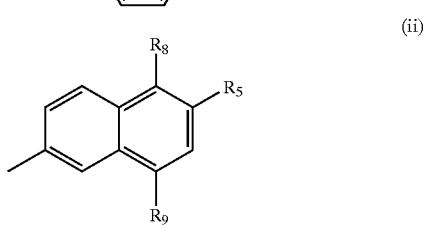

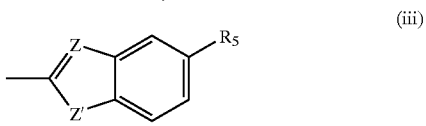

wherein
Y is a radical —CO—V—, —CH=CH—, —$CH_3$C=CH—, —CH=$CCH_3$—,

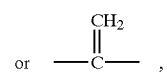

—CHOH—$CH_2$—O—,

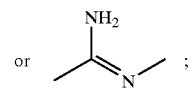

V is an oxygen atom (—O—), an aza radical (—NH—), a radical —CH=CH— or —C≡C—;
Z is a radical —CH— and Z' is an oxygen atom, or Z is a nitrogen atom (N) and Z' is an aza radical (—NH—);
$R_1$ is a hydrogen atom, halogen atom or a lower alkyl radical;
$R'_1$, is a hydrogen atom, halogen atom or a lower alkyl radical;
$R_2$ is a hydroxyl radical, halogen atom, an alkyl radical, optionally substituted by one or more hydroxyl or acyl groups, an alkoxyl radical, optionally substituted by one or more hydroxyl, alkoxyl or aminocarbonyl groups, and/or optionally interrupted by one or more oxygen atoms, an acyl radical or an aminocarbonyl radical, or a halogen;

$R_3$ is a hydrogen atom, halogen atom, a hydroxyl radical, an alkyl radical, or an alkoxyl radical;

$R_2$ and $R_3$ can form together a radical —O—$CH_2$—O—;

$R_4$ is a hydrogen atom, halogen atom, an alkyl radical, or an alkoxyl radical;

$R_5$ is a radical —CO—$R_{10}$ or an alkyl radical, optionally substituted by one or more hydroxyl groups, $R_6$ is a hydrogen atom, a halogen atom, preferably fluorine, an alkoxyl radical, or a hydroxyl group;

$R_7$ is a hydrogen atom or a halogen atom, preferably a fluorine atom;

$R_8$ is a hydrogen atom, a halogen atom or an alkyl radical;

$R_9$ is a hydrogen atom, a halogen atom or a hydroxyl radical;

$R_{10}$ is a hydroxyl radical, an alkoxy radical, a formula —Nr'r", wherein r' and r" represent a hydrogen atom, an optionally substituted aminoalkyl radical, a mono- or polyhydroxyalkyl radical, an optionally substituted aryl radical, or an amino acid or sugar residue, or alternatively, taken together, form a heterocycle, their pharmaceutically acceptable salts, or their optical and/or geometrical isomers thereof, with the proviso that such compounds do not include RAR-γ receptor-specific agonist ligands.

By RAR-γ receptor-specific agonist ligands in the subject application, it is intended ligands which possess a dissociation constant for ligands of the type RAR-α which is at least 10 times greater than the dissociation constant of these ligands for receptors of the type RAR-γ, and wherein such ligands further induce the differentiation of F9 cells.

All trans-retinoic acid and certain analogs thereof are known to be capable of inducing the differentiation of embryonic teratocarcinoma F9 cells cultured in the presence of agonists of RAR receptors. Also, the secretion of plasminogen activator is known to accompany this differentiation and is an indicator of the biological response of these cells to retinoids. (See *Skin Pharmacol.*, 3:256–267 (1994).)

Methods for measuring these dissociation constants are known in the art. For example, suitable methods are disclosed in the following references which are incorporated by reference herein. "Selective Synthetic Ligands for Nuclear Retinoic Acid Receptors Subtypes", in Retinoids, Progress in Research and Clinical Applications, Chapter 19 (pp 261–267), Marcel Dekker Inc., edited by Maria A. Livrea and Lester Packer; "Synthetic Retinoids: Receptor Selectivity and Biological Activity", in *Pharmacol. Skin*, Basal, Karger, 1993, Vol. 5:117–127; "Selective Synthetic Ligands for Human Nuclear Retinoic Acid Receptors", in *Skin Pharmacol.*, Vol. 5:57–65 (1992); "Identification of Synthetic Retinoids with Selectivity for Human Nuclear Retinoic Acid Receptor-γ", in Biochemical and Biophysical Research Communications, Vol. 186, No. 2, July 1992, pp 977–983; and "Selective High Affinity RAR-α or RAR-β Retinoic Acid Receptor Ligands", in *Molecular Pharmacology*, Vol. 40:556–562. See, also WO 97/13505, which discloses methods for identification of RAR-γ agonist ligands.

More preferably, the apoptosis inducing derivatives of formula (I) will have the formula (II):

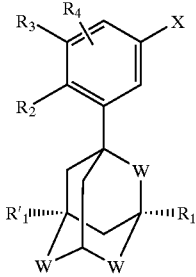

(II)

in which W, X, $R_1$, $R'_1$, $R_2$, $R_3$ and $R_4$ are defined above, and wherein such compounds do not include RAR-γ receptor-specific agonist ligands.

In one preferred embodiment, at least two of the radicals W are —$CH_2$—. Still more preferably, all of the W radicals are —$CH_2$—.

In another preferred embodiment, at least one of $R_1$ and $R_1'$ is a hydrogen atom. Still, more preferably, $R_1$ and $R_1'$ are both hydrogen atoms.

According to the invention, lower alkyl radical refers to a radical having from 1 to 6 carbon atoms, especially methyl, ethyl, propyl, isopropyl, butyl, tert-butyl and hexyl radicals.

Alkyl radical refers to a radical having 1 to 20 carbon atoms, straight chain or branched, especially methyl, ethyl, propyl, isopropyl, butyl, tert-butyl, hexyl, 2-ethylhexyl, octyl, dodecyl, hexadecyl and octadecyl radicals.

Acyl radical refers to a radical having 1 to 20 carbon atoms, straight chain or branched, containing a CO group, such as acetyl or benzoyl.

Alkoxy radical refers to a radical having 1 to 20 carbon atoms, straight chain or branched, containing an alkoxy group.

Sugar residue refers to a residue derived in particular from glucose, galactose or mannose or alternatively from glucuronic acid.

Monohydroxyalkyl radical refers to a radical having 1 to 6 carbon atoms, especially a hydroxymethyl, 2-hydroxyethyl, 2-hydroxypropyl, 3-hydroxypropyl, 4-hydroxybutyl, 5-hydroxypentyl or 6-hydroxyhexyl radical.

Polyhydroxyalkyl radical refers to a radical having 3 to 6 carbon atoms and 2 to 5 hydroxyl groups, especially a 2,3 dihydroxypropyl, 2,3,4-trihydroxybutyl or 2,3,4,5-tetrahydroxypentyl radical or a pentaerythritol residue.

Aryl radical refers to a phenyl radical optionally substituted by at least one halogen, a hydroxyl or a nitro functional group.

Aminoalkyl radical optionally substituted refers to an alkyl radical substituted by an amino residue, the amino residue may also be substituted by at least one alkyl radical, such as aminoethyl, methylaminoethyl, or dimethylaminoethyl radical.

Amino acid residue refers to a residue derived from any amino acid, such as lysine, glycine or aspartic acid.

Heterocycle preferably refers to a piperidino, morpholino, pyrrolidino, piperazine or homologs thereof, optionally substituted at the 4-position by a $C_1$–$C_6$ alkyl radical or a mono- or polyhydroxyalkyl radical as defined above.

Some compounds having the above generic formulae and their preparation have been disclosed in the following patent and patent applications incorporated herein by reference in their entirety: U.S. Pat. No. 4,740,519; U.S. Pat. No. 4,920,140; U.S. Pat. No. 5,059,621; U.S. Pat. No. 5,260,295; U.S. Pat. No. 5,428,052; U.S. Pat. No. 4,717,720; U.S. Pat. No. 4,940,696; U.S. Pat. No. 5,183,889; U.S. Pat. No. 5,212,303; U.S. Pat. No. Re 34440; U.S. Pat. No. 4,927,928; U.S. Pat. No. 5,200,550; U.S. Pat. No. 5,332,856; U.S. Pat. No. 5,468,897; U.S. Pat. No. 5,547,983; 1992; U.S. Pat. No. 5,476,860; U.S. Pat. No. 5,015,758; U.S. Pat. No. 5,183,889; FR 91 05394; French patent application No. 95 14260, filed on Dec. 1, 1995; and French patent application No. 95 14261, filed on Dec. 1, 1995.

Also, the present invention provides specific novel classes of adamantyl retinoid derivatives having the generic formulae set forth below, or their pharmaceutically acceptable salts, or optical and/or geometrical isomers thereof which induce apoptosis and/or which further comprise other desirable pharmacological properties:

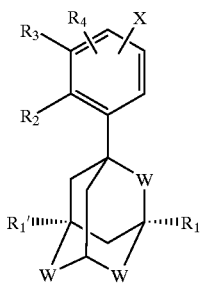

(I)

wherein $R'_1$, $R_1$, $R_2$, $R_3$, $R_4$, X and W are as defined supra, with the proviso that at least two of $R_2$, $R_3$ and $R_4$ are other than hydrogen; and with the further proviso that $R_2$ and $R_3$ cannot together form —O—CH$_2$—O—, or compounds of generic formula I, set forth below:

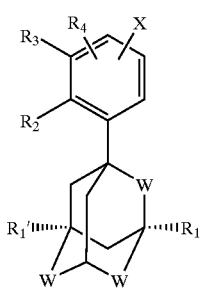

(I)

wherein W, X, $R_1'$, $R_1$, $R_2$, $R_3$, $R_4$, $R_5$, $R_6$, $R_7$, $R_8$, $R_9$, $R_{10}$, Y, V are as defined supra, except with the proviso that at least one of W is —O—, —S—, —SO— or —SO$_2$ and/or at least one of $R_1$ and $R_1'$ is halogen or a lower alkyl radical, preferably, wherein at least one of W is —O— and/or $R_1$ is a lower alkyl radical and/or $R_1'$ is a lower alkyl radical, and/or also preferably wherein X comprises formula (ii), and/or $R_8$ is preferably hydrogen and/or $R_9$ is hydrogen and/or $R_5$ is —CO—$R_{10}$; or compounds of generic formula I, set forth below:

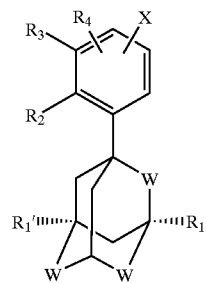

(I)

wherein W, X, $R_1'$, $R_1$, $R_2$, $R_3$, $R_4$, $R_5$, $R_6$, $R_7$, $R_8$, $R_9$, $R_{10}$, Y, V are as defined supra, except with the proviso that $R_5$ is —CO—$R_{10}$, and $R_{10}$ is a radical of formula Nr'r'', wherein at least one of r' and r'', is hydrogen and the other is an optionally substituted aminoalkyl radical, or alternatively r' and r'', taken together, form a heterocycle, preferably a piperazino or a homolog thereof, preferably wherein X comprises formula (ii) and/or more preferably $R_8$ is hydrogen and/or $R_9$ is hydrogen. Also, preferred are compounds of formula (I) wherein $R_2$ is an alkoxy radical or hydroxyl group and/or $R_3$ is hydrogen and/or $R_4$ is hydrogen and/or $R_2$ and $R_3$ together form —O—CH$_2$—O—;

or compounds of formula (III):

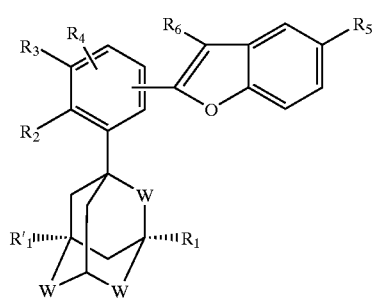

(III)

wherein $R'_1$, $R_1$, $R_2$, $R_3$, $R_4$, $R_5$ and $R_6$ and W are as defined supra;

A more specific subclass of compounds of formula (I) comprises compounds of formula (II) below:

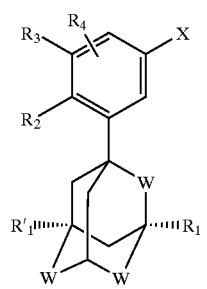

(II)

wherein $R_1'$, $R_1$, $R_2$, $R_3$, $R_4$, X and W are as defined above and at least two of $R_2$, $R_3$ and $R_4$ are not hydrogen, and wherein $R_2$ and $R_3$ cannot together form —O—CH$_2$—O; or compounds of formula (II) wherein $R_5$ is —C—O—$R_{10}$, $R_{10}$ is a radical of formula —Nr'r", wherein one of r' and r" is hydrogen and the other is an optionally substituted aminoalkyl radical, or alternatively r' and r" taken together form a heterocycle, preferably piperazino or a homolog thereof, and wherein preferably $R_8$ is hydrogen and/or $R_9$ is hydrogen; or compounds of formula (II) where at least one of W is —O—, —S—, —SO— or —SO$_2$ and/or at least one of $R_1$ and $R_1'$ is halogen or a lower alkyl radical, wherein X preferably has formula (ii), and more preferably $R_8$ is hydrogen and/or $R_9$ is preferably hydrogen and/or $R_5$ is —CO—$R_{10}$.

Also preferred are compounds of formula (II) wherein $R_2$ is an alkoxy radical or hydroxyl group and/or $R_3$ is hydrogen and/or $R_4$ is hydrogen and/or $R_2$ and $R_3$ together form —O—CH$_2$—O—.

An even more specific subclass of novel retinoid related compounds of formula (II) comprises adamantyl retinoid related compounds having the generic formula set forth below.

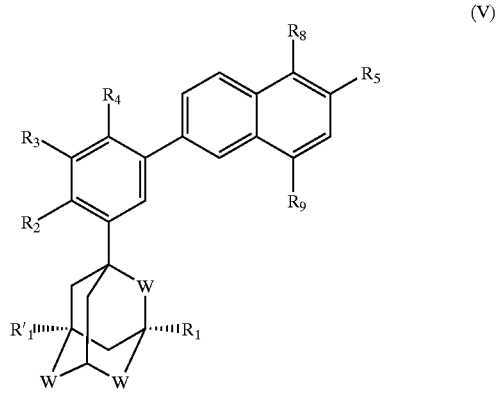

(V)

wherein $R'_1$, $R_1$, $R_2$, $R_3$, $R_4$, $R_5$, $R_6$, $R_7$, $R_8$, $R_9$ and W are as defined supra, with the proviso that at least two of $R_2$, $R_3$ and $R_4$ are other than hydrogen, and with the further proviso that $R_2$ and $R_3$ cannot together form —O—CH$_2$—O—.

Preferred compounds of formula (V) comprise retinoid related compounds wherein $R_5$ is a hydroxycarbonyl radical, preferably —CO—$R_{10}$, and/or compounds wherein $R_2$ is a hydroxyl radical, an alkoxyl radical, and/or $R_8$ is hydrogen, and/or $R_9$ is hydrogen and/or $R_3$ is a hydroxyl radical or alkoxyl radical, and/or $R_4$ is hydrogen or an alkyl radical.

Other preferred compounds of formula (V) include compounds wherein at least one of W is —O—, —S—, —SO— or —SO$_2$— and/or at least one of $R_1$ and $R_1'$ is halogen or a lower alkyl radical.

The novel retinoid derivatives of the present invention can be synthesized by known methods for synthesizing retinoids such as are disclosed in the patents and applications incorporated by reference herein. Further, specific methods for the synthesis of the retinoids of formula (V) are described below.

SCHEME I

According to synthetic Scheme I a halobenzene derivative (1) (see schematic of Scheme I infra) is coupled to a naphthyl halide or 2-naphthyl trifluoromethanesulfonate (2) to form (3), e.g., through treatment of (1) in dry THF with butyl lithium at −78° C. followed by zinc chloride, followed by (2) in the presence of nickel bis(diphenylphosphino) ethane dichloride. A tertiary ester or halide derived from an oxaadamantyl, adamantyl, thiaadamantyl or related molecule of formula (4) is then reacted with (3) in the presence of 0.1 to 1.3 molar equivalents of an appropriate acid (e.g., sulfuric acid or trifluoromethylsulfonic acid if X3 is acetoxy or mesyloxy) in a mixed solvent, preferably containing cyclohexane and either heptane, dichloromethane, or 1,2-dichloroethane at a temperature between 25° C. and 90° C.

Esters obtained in accordance with the above methods wherein $R_5$ is an ester group may be converted, according to known procedures, into various analogs which are the objects of meanings for the radical $R_5$. For example, such esters include saponified acids which can be transformed into acid chlorides which are easily converted into amides. Alternatively, such amides can be obtained by the direct action of amines on the esters obtained as described above. Moreover, the reduction of the esters, aldehydes or amides by an appropriate reducing agent (for example lithium aluminohydride) further permits the production of the corresponding alcohols and amines.

The subject synthetic method is especially preferred if $R_2$ is an alkoxy or hydroxy group and $R_5$, $R_8$ and $R_9$ are not strongly electron-donating groups such as alkoxy, hydroxy or alkamino, and all of the functionalities other than $R'_1$, $R_1$, and W are compatible with butyl lithium or can be used in a protected form that is compatible with butyl lithium.

SCHEME I

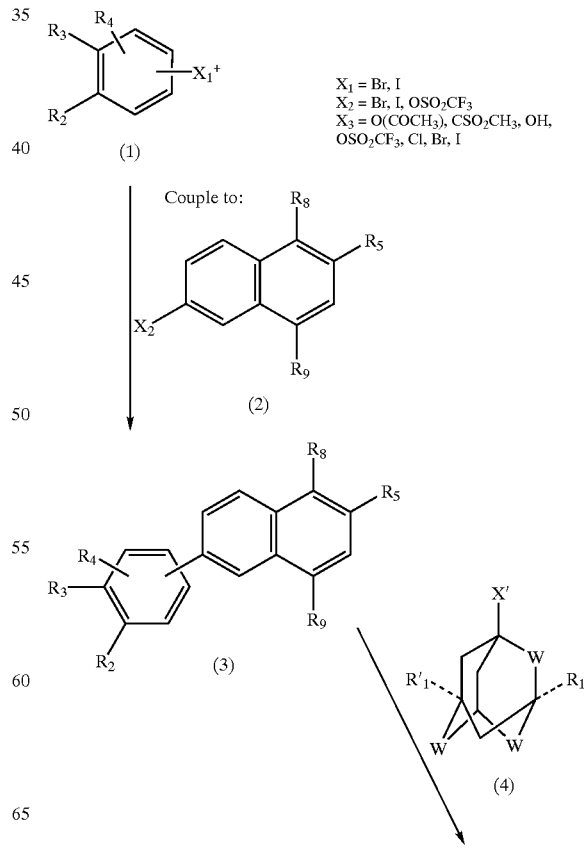

$X_1$ = Br, I
$X_2$ = Br, I, OSO$_2$CF$_3$
$X_3$ = O(COCH$_3$), CSO$_2$CH$_3$, OH, OSO$_2$CF$_3$, Cl, Br, I

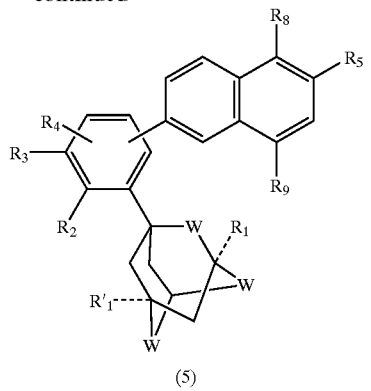

(5)

SCHEME II

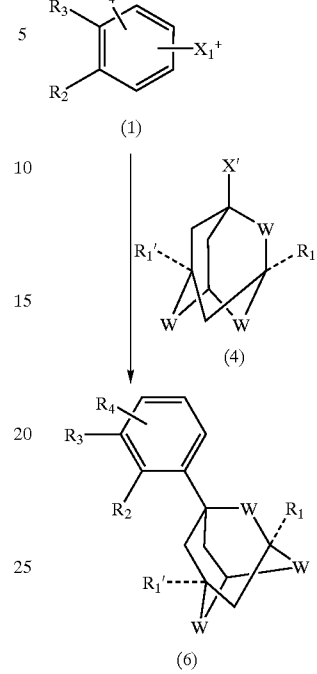

A second method (Scheme II) for synthesizing the novel adamantyl retinoids of formula (V) is shown in Scheme II. This method comprises reacting a tertiary ester or halide derived from an oxaadamantyl, adamantyl, thiaadamantyl or related molecule of formula (3) with a halobenzene derivative (1) in the presence of 0.1 to 1.3 molar equivalents of an appropriate acid (sulfuric acid or trifluoromethylsulfonic acid if $X_3$ is acetoxy, hydroxy or mesyloxy) in a mixed solvent containing cyclohexane and either heptane, dichloromethane, or 1,2-dichloroethane at a temperature between 25 and 90° C. The resulting adduct (6) is then coupled to the 2-naphthyl halide or 2-naphthyl trifluoromethanesulfonate (2) to form (5), e.g., through treatment of (6) in dry THF with butyl lithium at −78° C. followed by zinc chloride, followed by (2) in the presence of nickel bis(diphenylphosphino)ethane dichloride.

Esters obtained in accordance with the methods described above wherein $R_5$ is an ester group may be converted, according to known procedures, into various analogs which are provided for based on the definition of the $R_5$ radical in generic formula (V). For example, such esters include saponified acids which can be transformed into acid chlorides which in turn are easily converted into amides. Alternatively, such amides can be obtained by the direct action of amines on the esters obtained earlier. The reduction of the esters, aldehydes or amides by an appropriate reducing agent (for example, lithium aluminohydride) further permits production of the corresponding alcohols and amines.

This synthetic scheme is preferred if $R_5$, $R_8$ and/or $R_9$ are strongly electron-donating groups such as alkoxy, hydroxy or alkamino, and all of the functionalities are compatible with butyl lithium or can be used in a protected form that is compatible with butyl lithium.

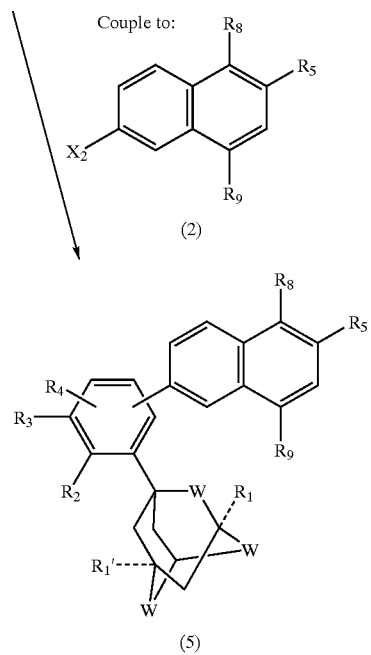

The subject adamantyl retinoid derivatives identified supra which induce apoptosis may be used for the treatment of many different cancers. Specific examples of cancers treatable with the subject retinoid derivatives include by way of example bladder cancer, brain cancer, head and neck cancer, kidney cancer, lung cancers such as small cell lung cancer and non-small cell lung cancer, myeloma, neuroblastoma/glioblastoma, ovarian cancer, pancreatic cancer, prostate cancer, skin cancer, liver cancer, melanoma, colon cancer, cervical carcinoma, breast cancer, and leukemias. Moreover, because of their apoptosis inducing activity, the subject adamantyl retinoid derivatives are especially well suited for treatment of solid tumors and advanced cancers which cannot be treated by most conventional cancer therapies.

In treating cancer, the adamantyl or adamantyl derivative compounds of the present invention may be administered by any pharmaceutically acceptable means, e.g., systemically, enterally, parenterally or topically. An effective therapeutic dosage will comprise a dosage sufficient to induce apoptosis of cancer cells. This dosage will vary dependent upon factors such as the condition of the patient treated, the specific compound, whether it is used alone or in combination with other therapies, among other factors. In general, an effective dosage will vary from 0.01 mg/kg to 100 mg/kg of body weight, and more preferably 1 mg to 50 mg of body weight, typically administered at the rate of 1 to 3 dosages per diem.

As discussed, the adamantyl retinoid derivatives according to the invention which induce apoptosis are useful for treating many different types of cancers. Specific adamantyl retinoid compounds according to the invention which have been demonstrated to exhibit such activity are set forth in Table I. The specific types of cancers that these compounds have been shown to be active against are also identified.

TABLE I

LIST OF ACTIVE COMPOUNDS

| | Compound Name | Types of Cancers and Precancers Active Against |
|---|---|---|
| 1 | 6-[3-(1-adamantyl)-4-methoxyphenyl]-2-naphthoic acid | brain, cervical (including, e.g., cervical intraepithelial neoplasia I, II, III), head and neck, leukemia, lymphoma, prostate, skin |
| 2 | 2-[3-(1-adamantyl)-4-methoxyphenyl]-5-benzimidazole carboxylic acid | brain, colon, leukemia, lung, cervical (including, e.g., cervical intraepithelial neoplasia I, II, III), lymphoma, myeloma, ovarian, pancreatic, prostate, skin, liver |
| 3 | 6-[3-(1-adamantyl)-4-hydroxymethylphenyl]-2-naphthoic acid | bladder, brain, breast, cervical, colon, head and neck, leukemia, kidney, lung, myeloma, ovarian, pancreatic, prostate, skin, liver |
| 4 | 6-[3-(1-adamantyl)-4-hydroxy-5-methoxyphenyl]-2-naphthoic acid | brain, breast, kidney, lung, leukemia, lymphoma, myeloma, ovarian, pancreatic, prostate, skin, liver |
| 5 | 6-[3-(1-adamantyl)-4-acetoxymethylphenyl]-2-naphthoic acid | head and neck, leukemia, lung, lymphoma, myeloma, pancreatic, skin |
| 6 | 6-[3-(1-adamantyl)-4,5-methylenedioxyphenyl]-2-naphthoic acid | brain, breast, head and neck, kidney, leukemia, lung, lymphoma, myeloma, ovarian, prostate, skin, liver, cervical (including, e.g., cervical intraepithelial neoplasia I, II, III), |
| 7 | N-{6-[3-(1-adamantyl)-4-methoxyphenyl]-2-naphthalenecarboxoyl}piperizide | brain, breast, head and neck, myeloma, prostate, skin |
| 8 | 4-{3-oxo-3-[3-(1-adamantyl)-4-methoxyphenyl]-1-propynyl}benzoic acid | brain, breast, leukemia, lung, lymphoma, skin, liver |
| 9 | 4-[N-(3-(1-adamantyl)-4-methoxybenzoyl)amido]2-methoxybenzoic acid | head and neck, kidney, ovarian, skin |
| 10 | 2-[3-(1-adamantyl)-4-methoxyphenyl]-5-methylbenzimidazole | leukemia, lymphoma, myeloma |
| 11 | 6-[3-(1-adamantyl)-4-(1,2-dihydroxyethyl)phenyl]-2-naphthoic acid | brain, breast, leukemia, pancreatic, skin |
| 12 | 6-[3-(1-adamantyl)-4-hydroxy-6-methylphenyl]-2-naphthoic acid | head and neck, leukemia, pancreatic |
| 13 | 6-[3-(1-adamantyl)-4-methoxy-6-methylphenyl]-2-naphthoic acid | brain, head and neck, leukemia, pancreatic |
| 14 | 6-[3-(1-adamantyl)-4-hydroxyphenyl]-2-hydroxymethylnaphthalene | bladder, kidney, skin |
| 15 | 4-[3-(1-adamantyl)-4-methoxybenzyloxy]benzoic acid | breast, leukemia, prostate |
| 16 | 2-[3-(1-adamantyl)-4-methoxyphenyl]-5-benzofurancarboxylic acid | brain, breast, prostate |
| 17 | 6-[3-(1-adamantyl)-4-hydroxyphenyl]-2-naphthoic acid methyl ester | leukemia |
| 18 | 1-methyl-4-hydroxy-6-[3-(1-adamantyl)-4-methoxyphenyl]-2-naphthoic acid methyl ester | lymphoma, liver |
| 19 | N-{4-[N-(3-(1-adamantyl)-4-methoxybenzoyl)amido]benzoyl}morpholide | kidney, myeloma, prostate, skin |
| 20 | 4-[3-(1-adamantyl)-4-methoxybenzoyloxy]-2-fluorobenzoic acid | lymphoma, skin |
| 21 | 4-hydroxycarbonyl-2-fluorophenyl ester of 3-(1-adamantyl)-4-methoxybenzoic acid | leukemia |

TABLE I-continued

LIST OF ACTIVE COMPOUNDS

| | Compound Name | Types of Cancers and Precancers Active Against |
|---|---|---|
| 22 | 6-[3-(1-adamantyl)-4-ethylphenyl]-2-naphthoic acid | breast, leukemia, myeloma |
| 23 | 6-[3-(1-adamantyl)-4-(3-hydroxy-propoxy)phenyl]-2-naphthoic acid | breast, leukemia, lymphoma |
| 24 | 6-[3-(1-adamantyl)-4-aminocarbonylphenyl]-2-naphthoic acid | leukemia, lymphoma |
| 25 | N-(4-carboxyphenyl)-3-(1-adamantyl)-3-oxopropionamide | lymphoma |
| 26 | 2-hydroxy-4-{2-[3-(1-adamantyl)-4-methoxyphenyl]-2-hydroxyethoxy}benzoic acid | lymphoma |
| 27 | (S)-6-[3-(1-adamantyl)-4-(2S,3-dihydroxypropoxy)phenyl]-2-naphthoic acid | leukemia |
| 28 | (E) 4-{3-oxo-3-[3-methoxy-4-(1-adamantyl)phenyl]prop-1-enyl}benzoic acid | leukemia |
| 29 | (E) 4-{3-oxo-3-[4-(2-methoxyethoxy-methoxy)-3-(1-adamantyl)phenyl]prop-1-enyl}benzoic acid | brain, leukemia, lung, lymphoma, prostate |
| 30 | (E) 4-{2-[4-(6-aminocarbonylpentyloxy)-3-(1-adamantyl)phenyl]ethenyl}benzoic acid | lymphoma, myeloma |
| 31 | 3-(1-adamantyl)-4-methoxy-N-(4-carboxyphenyl)benzamidine | leukemia |
| 32 | 4"-Erythromycin A ester of 6-[3-(1-adamantyl)-4-methoxyphenyl]2-naphthoic acid | leukemia, lymphoma |
| 33 | 4-carboxyphenyl ester of 3-(1-adamantyl)-4-(2,3-dihydroxyproproxy)benzoic acid | leukemia, skin |
| 34 | 6-[3-(1-adamantyl)-4-(2,3-dihydroxy-propoxy)phenyl]-2-naphthoic acid | leukemia, skin |
| 35 | N-4-carboxyphenyl 3-(1-adamantyl)-4-(methoxycarbonyl)benzamide | leukemia, lymphoma, myeloma |
| 36 | 6-[3-(1-adamantyl)-4,5-dihydroxyphenyl]-2-naphthoic acid | brain, head and neck, leukemia, lymphoma, myeloma, pancreatic |
| 37 | 6-[3-(3-methyl-1-adamantyl)-4,5-methylenedioxyphenyl]-2-naphthoic acid | kidney, leukemia, lung, lymphoma, skin |
| 38 | 6-[3-(2-oxa-1-adamantyl)-4,5-methylenedioxyphenyl]-2-naphthoic acid | leukemia, skin |
| 39 | 6-[3-(2-oxa-1-adamantyl)-4-methoxyphenyl]-2-naphthoic acid | kidney, lymphoma, skin, liver |
| 40 | 6-[3-(2-oxa-3-methyl-1-adamantyl)-4-methoxyphenyl]-2-naphthoic acid | bladder, breast, kidney, leukemia, lung, lymphoma, ovarian, prostate, skin |
| 41 | 6-[3-(3-methyl-1-adamantyl)-4-methoxyphenyl]-2-naphthoic acid | skin |
| 42 | 6-[3-(3,5-dimethyl-1-adamantyl)-4-methoxyphenyl]-2-naphthoic acid | skin |
| 43 | 6-[3-(3,5-dimethyl-1-adamantyl)-4,5-methylenedioxyphenyl]-2-naphthoic acid | prostate, breast, neuroblastoma |
| 44 | N-{6-[3-(1-adamantyl)-4-methoxyphenyl]-2-naphthalenecarboxoyl}homopiperazide | bladder, kidney, epidermal, leukemia lung, neuroblastoma, hepatoma, cervix, skin |
| 45 | N-(2-aminoethyl)-{6-[3-(1-adamantyl)-4-methoxyphenyl]-2-naphthalenecarboxamide] | bladder, kidney, prostate, leukemia, breast, lung, neuro-blastoma, hepatoma, pancreas, cervix skin |
| 46 | N-{6-[3-(1-adamantyl)-4,5-methylenedioxy]-2-naphthalenecarboxoyl}piperazide | prostate, neuroblastoma, hepatoma |
| 47 | N-{6-[3-(1-adamantyl)-4,5-methylenedioxy]-2-naphthalenecarboxoyl}homopiperazide | bladder, neuroblastoma, cervix, skin |
| 48 | N-(2-aminoethyl)-{6-[3-(1-adamantyl)-4,5-methylenedioxyphenyl]-2-naphthalenecarboxamide} | breast, hepatoma, skin |
| 49 | 6-[3-(3-methyl-1-adamantyl)-4-hydroxyphenyl]-2-naphthalenecarboxylic acid | breast, neuroblastoma, leukemia |

As can be seen from the above, the subject adamantyl retinoids exhibit a broad range of activity against numerous different types of cancers.

Moreover, the present invention also relates to the usage of the specific novel classes of adamantyl retinoid compounds identified supra for other therapeutic as well as cosmetic usages.

Depending on the nature of the radicals used, the subject adamantyl or adamantyl derivative containing retinoid compounds should exhibit either an agonist activity in the test for differentiation of embryonic teratocarcinoma cells (F9) in mice (*Cancer Research*, 43, p. 5268 (1983)) and/or in the test for inhibition of ornithine decarboxylase after induction by TPA in mice (*Cancer Research*, 38, p. 793–801 (1978)) or, in contrast, an antagonist activity with respect to the expression of one or more biological markers in the test for differentiation of embryonic teratocarcinoma cells (F9) in mice (*Skin Pharmacol.*, 3, pp. 256–267 (1990)) and/or for the in vitro differentiation of human keratinocytes (*Anal. Biochem.*, 192, pp. 232–236 (1991)).

Based on these properties, the novel adamantyl or adamantyl derivative containing retinoid compounds according to the invention are well suited in the following fields of therapy:

(1) for treating dermatological conditions associated with a keratinization disorder related to differentiation and proliferation, in particular for treating acne vulgaris, comedonic or polymorphic acne, acne rosacea, nodulocystic acne, acne conglobate, senile acne and secondary acnes such as solar, drug or occupational acne;

(2) for treating other types of keratinization disorders, in particular ichthyoses, ichthyosiform conditions, Darier's disease, palmoplantar keratoderma, leukoplakia and leucoplakiform conditions or cutaneous or mucosal (oral) lichen;

(3) for treating other dermatological conditions associated with a keratinization disorder manifesting an inflammatory and/or immunoallergic component and, in particular, all forms of psoriasis, whether cutaneous, mucosal or ungual, and even psoriatic rheumatism, or alternatively cutaneous or skin atopy, such as eczema, or respiratory atopy or alternatively gingival hypertrophy; the compounds can also be used in certain inflammatory conditions not exhibiting keratinization disorder;

(4) for treating all dermal or epidermal proliferations, whether benign or malignant, whether or not of viral origin, such as common warts, flat warts and epidermodysplasia verruciformis, florid oral papillomatoses and the proliferations which can be induced by ultraviolet radiation, in particular in the case of basal cell and prickle cell epithelioma;

(5) for treating other dermatological disorders, such as bullous dermatoses and collagen diseases;

(6) for treating certain ophthalmological disorders, in particular corneopathies;

(7) for repairing or controlling aging of the skin, whether photoinduced or chronologic, or for reducing actinic keratoses and pigmentations, or any pathology associated with chronologic or actinic aging;

(8) for preventing or treating the stigmata of epidermal and/or dermal atrophy induced by local or systemic corticosteroids, or any other form of cutaneous atrophy;

(9) for preventing or treating disorders of healing, or for preventing or for repairing stretch marks;

(10) for controlling disorders of the sebaceous function, such as hyperseborrhoea of acne or simple seborrhoea;

(11) for the prevention of cancerous or precancerous conditions;

(12) for the treatment of inflammatory conditions such as arthritis;

(13) for the treatment of any condition of viral origin at the cutaneous or general level;

(14) for the prevention or treatment of alopecia;

(15) for the treatment of dermatological or general conditions including an immunological component;

(16) for the treatment of ailments of the cardiovascular system, such as arteriosclerosis, and myocardial infarction; and

(17) for the treatment or prevention of osteoporosis.

For the aforesaid therapeutic or pharmaceutical applications, the novel compounds according to the invention can advantageously be used in combination with other compounds displaying a retinoid-type activity, with vitamins D or derivatives thereof, with corticosteroids, with compounds which control free radicals, α-hydroxy or α-keto acids or derivatives thereof, or alternatively with ion channel blockers.

By "vitamins D or derivatives thereof" are intended, for example, derivatives of vitamin $D_2$ or $D_3$ and in particular 1,25-dihydroxyvitamin $D_3$. By "compounds which control free radicals" are intended, for example, α-tocopherol, superoxide dismutase, ubiquinol or certain metal chelating agents.

By "α-hydroxy or α-keto acids or derivatives thereof" are intended, for example, lactic, malic, citric, glycolic, mandelic, tartaric, glyceric or ascorbic acids or salts, amides or esters thereof.

By "ion channel blockers" are intended, for example, Minoxidil (2,4-diamino-6-piperidinopyrimidine 3-oxide) and derivatives thereof.

The present invention thus also features medicinal compositions containing at least one of the above-identified novel adamantyl retinoid compounds, one of its chiral or geometric isomers, or one of its pharmaceutically acceptable salts, or other derivatives thereof.

The pharmaceutical/therapeutic compositions of the present invention, intended especially for treating the aforesaid disease states comprise a pharmaceutically acceptable vehicle, carrier or diluent which is compatible with the mode or regime of administration selected for the given composition and at least one novel adamantyl compound according to the invention or one of its chiral or geometric isomers, or a pharmaceutically acceptable salt thereof.

The administration of the compounds according to the invention can be carried out by any suitable means of administration, e.g., systemically, enterally, parenterally, topically or ocularly.

For enteral administration, the medicinal/pharmaceutical compositions may be in the form of tablets, hard gelatin capsules, dragees, syrups, suspensions, solutions, elixirs, powders, granules, emulsions or polymeric or lipid microspheres or nanospheres or vesicles which permit a controlled release. For parenteral administration, the compositions may be in the form of solutions or suspensions for perfusion or for injection.

Effective dosage of a novel retinoid compound according to the invention in the above-identified therapies may be determined by well known methods. In general, the compounds according to the invention are administered at a daily dose of approximately 0.01 mg/kg to 100 mg/kg by body weight, and at the rate or regime of 1 to 3 doses per diem.

For topical administration, the pharmaceutical compositions based on novel compounds according to the invention are more particularly intended for treating the skin and the mucosal membranes and can then be provided in the form of ointments, creams, milks, salves, powders, impregnated pads, solutions, gels, sprays, lotions or suspensions. They can also be provided in the form of polymeric or lipid vesicles or nanospheres or microspheres or of polymeric patches and of hydrogels which permit controlled release. These compositions for topical administration can, moreover, be provided either in anhydrous form or in an aqueous form, according to the particular clinical indication.

In a preferred embodiment, the compositions will be in the form of an aqueous gel formulation administrable in combination with a cervical cap and collagen sponge wherein the cervical cap is constitute of rubber, silicone or other suitable polymeric materials.

For ocular administration, they are principally eye washes.

These compositions for a topical or ocular application contain at least one novel adamantyl retinoid according to the invention, or one of its optical or geometric isomers or, alternatively one of its salts, at a concentration preferably ranging from 0.001% to 5% by weight relative to the total weight of the composition.

As discussed, the novel adamantyl compounds according to the invention also find application in the cosmetics field, in particular for body and hair care/hygiene, and especially for the treatment of skins tending to develop acne, for hair regrowth and combating hair loss, for combating the greasy appearance of the skin or the hair, for protecting against the deleterious effects of sunlight or in the treatment of physiologically dry skin, and for preventing and/or for controlling photoinduced or chronologic aging.

For cosmetic applications, the novel compounds according to the invention can, moreover, be advantageously be used in combination with other compounds displaying a retinoid-type activity, with vitamin D or derivatives thereof, with corticosteroids, with compounds which control free radicals, with α-hydroxy or α-keto acids or derivatives thereof, or alternatively with ion channel blockers, all of these various active agents being as defined above.

The present invention therefore also features cosmetic compositions comprising a cosmetically acceptable vehicle, carrier or diluent which is suitable for topical application, at least one of the novel adamantyl retinoid compounds identified supra or one of its chiral or geometric isomers, or one of its salts, etc. Such cosmetic compositions are advantageously in the form of a cream, milk, lotion, ointment, gel, polymeric or lipid vesicles or nanospheres or microspheres, soap or shampoo.

The concentration of the retinoid compound in the cosmetic compositions according to the invention advantageously ranges from 0.001% and 3% by weight relative to the total weight of the composition.

The medicinal and cosmetic compositions according to the invention can, in addition, contain inert or even pharmacodynamically or cosmetically active additives or combinations of these additives, and, especially: wetting agents; depigmenting agents such as hydroquinone, azelaic acid, caffeic acid or kojic acid; emollients; hydrating or moisturizing agents such as glycerol, PEG 400, thiamorpholinone and its derivatives or alternatively urea; anti-seborrhoeic or anti-acne agents such as S-carboxymethylcysteine, S-benzylcysteamine, their salts or derivatives thereof, or benzoyl peroxide; antibiotics such as erythromycin and esters thereof, neomycin, clindamycin and esters thereof, or tetracyclines; anti-fugal agents such as ketoconazole or 4,5-polymethylene-3-isothiazolidones; agents promoting hair regrowth, such as Minoxidil (2,4-diamino-6-piperidinopyrimidine 3-oxide) and derivatives thereof, Diazoxide (7-chloro-3-methyl-1,2,4-benzothiadiazine 1,1-dioxide) and phenytoin (5,5-diphenylimidazolidine-2,4-dione); non-steroidal anti-inflammatory agents; carotenoids and especially β-carotene; anti-psoriatic agents such as anthralin and its derivatives; and, lastly, eicosa-5,8,11,14-tetraynoic and eicosa-5,8,11-triynoic acids, and esters and amides thereof.

The compositions according to the invention can also contain flavor-enhancing agents, preservatives such as the esters of para-hydroxybenzoic acid, stabilizing agents, moisture-regulating agents, pH-regulating agents, osmotic-pressure-modifying agents, emulsifying agents, UV-A and UV-B screening agents and antioxidants such as α-tocopherol, butylated hydroxyanisole or butylated hydroxytoluene.

In order to further illustrate the present invention and the advantages thereof, the following specific examples are given, it being understood that same are intended only as illustrative and in nowise limitative.

EXAMPLES

The following examples relate to synthesis of specific adamantyl retinoid related compounds. All starting materials were obtained from Aldrich Chemical Company except for the methyl ester of 6-(4-methoxyphenyl)naphthoic acid (which was synthesized according to U.S. Pat. No. 5,015, 758) and 3-methyl-2-oxa-1-adamantanol (which was synthesized according to Stetter, *Chemische Berichte*, 99, p. 1435 (1966)).

Example 1

Synthesis 2-Oxa-1-adamantanol 386.6 mg (2.54 mmoles) of bicyclo[3.3.1]nonane-3,7-dione is dissolved in 5 mL of methanol and treated with sodium borohydride (100 mg, 2.64 mmoles) at 0° C. for 2 hours. The solution is treated with 5 mL of saturated aqueous sodium bicarbonate for 1 hour at 25° C. and extracted with 3×10 mL portions of chloroform. The combined chloroform extracts are combined, dried over sodium sulfate, stripped of solvent in vacuo, and purified by column chromatography (silica, eluant=50% hexanes, 50% ethyl acetate) yielding 343 mg (88%) of the desired product. $^1$HNMR (CDCl$_3$, 500 Mhz): d 1.563 (d, 2H), 1.70–1.76 (m, 1H), 1.788 (d, 2H, J=11.1 Hz), 1.839 (d, 2H, J=13.1 Hz), 1.925 (d, 2H, J=13.0 Hz), 2.310 (s, 2H), 2.690 (s, 1H), 4.283 (s, 1H).

Example 2

Synthesis of 3-Methyl-1-adamantyl Acetate 121 mg (0.728 mmoles) of 3-methyl-1-adamantanol are dissolved in 0.2 mL n-heptane and 0.2 mL cyclohexane. A mixture of 0.2 mL (2.25 mmoles) of acetic anhydride and 2 microliters (0.036 mmoles) of concentrated sulfuric acid is added, and the mixture is stirred at ambient temperature for 20.5 hours. The solution is dissolved in 10L of ether and extracted with 10 mL of water. The aqueous layer is extracted with 10 mL ether. The ether layers are combined, extracted with 2×mL of water followed by 40 mL of aqueous sodium bicarbonate (10 g/liter), dried over magnesium sulfate, and stripped of solvent in vacuo. The product is a colorless oil with Rf 0.55 (silica: eluant hexane 75%, ethyl acetate 25%).

Example 3

Synthesis of 3,5-Dimethyl-1-adamantyl Acetate 2.486 (10.2 mmoles) of 3,5-dimethyl-1-bromoadamantane is refluxed for 16 hours with 2.034 g (20.7 mmoles) of potassium acetate in 10 mL of acetic acid. The solution is poured over 100 grams of ice, allowed to melt, and extracted with 3×10 mL of diethyl ether. The combined ether extracts are washed with saturated aqueous sodium bicarbonate followed by saturated aqueous sodium chloride, then dried over sodium sulfate. The solvent is removed under vacuum, yielding 1.521 (67%) of the desired product, a colorless oil. TLC: Rf=0.68 (silica plate: eluant hexane 90%, ethyl acetate 10%). $^1$HNMR (CDCl$_3$, 500 Mhz): 0.858 (s, 6H), 1.115 (d, 2H, J=12.4 Hz), 1.177 (d, 2H, J=12.4 Hz), 1.260 (d, 2H, J=12.3 Hz), 1.367 (d, 2H, J=12.3 Hz), 1.714 (d, 2H, J=11.6 Hz), 1.766 (d, 2H, J=11.6 Hz), 1.939 (s, 2H), 1.976 (s, 3H), 2.191 (m, 1H).

Example 4

Synthesis of 2-Oxa-1-adamantyl Mesylate 340 mg (2.21 mmoles) of 2-oxa-1-adamantanol (see Example 1) and 20 mg (0.163 mmoles) of 4-dimethylaminopyridine are dissolved in 5 mL of dry pyridine under argon at −40° C. A suspension of 565 mg (3.25 mmoles) of methanesulfonic anhydride in 8 mL of dry pyridine is added at −40° C. The rest of solid methanesulfonic anhydride was added into the reaction flask. The mixture is stirred at 0° C., and allowed to warm to 25° C. over 18 hours. After removing the solvent in vacuo, the residue was dissolved in 20 mL dichloromethane, washed with 10 mL of water, and dried to yield 512 mg (100%) of the desired product. Rf=0.50 (50% ethyl acetate in hexanes). $^1$HNMR (CDCl$_3$, 500 Mhz): d 1.594 (d, 2H, J=13.0 Hz), 1.76–1.86 (m, 2H), 2.010 (d, 4H, J=12.5 Hz), 2.330 (d, 2H, J=11.9 Hz), 2.380 (s, 2H), 3148 (s, 3H), 4.439 (s, 1H).

Example 5

Synthesis of 3-Methyl-2-oxa-1-adamantyl Mesylate

A mixture of 230 mg (1.37 mmoles) of 3-methyl-2-oxa-1-adamantanol, 20 mg (0.163 mmoles) of 4-dimethylaminopyridine, and 350 mg (2.0 mmoles) of methanesulfonic anhydride is treated with 10 mL of dry pyridine under argon at −40° C. The reaction mixture is warmed to 0° C. and allowed to gradually warm to 25° C. over 13 hours. The solvent is removed in vacuo, and the residue dissolved in 20 mL dichloromethane, washed with 10 mL of water, dried over sodium sulfate, and stripped of solvent in vacuo, yielding 341 mg of crude (approximately 95% pure) product. TLC: Rf=0.75 (Silica: 50% hexanes, 50% ethyl acetate).

Example 6

Synthesis of Methyl Ester of 6-(3,4-Methylenedioxyphenyl)-2-naphthoic Acid

Magnesium turnings (1.48 g, 61 mmoles) were placed in a 250 mL three-neck flask attached to a reflux condenser. The flask was evacuated under vacuum with heatgun. Argon and dry THF (100 mL) were introduced. 5-Bromo-1,3-benzodioxole (6.0 mL, 10.0 g, 49.8 mmoles) was added and the mixture was heated at 80° C. oil bath. A few minutes later the reaction was initiated and the mixture was refluxed for 3 hr. A portion of such Grignard solution (50 mL, 24.9 mmole) was added into a solution of anhydrous zinc chloride (3.46 g, 24.9 mmole) in dry THF (40 mL) and the resulting mixture was stirred for 30 minutes at room temperature. The organozinc solution was transferred into a flask containing 1,-bis(diphenylphosphono)ethane dichloronickel(II) (400 mg) and methyl 6-bromo-2-naphthoate (5.23 g, 19.9 mmole) in dry THF (40 mL). The reaction solution was stirred at room temperature for 18 hours. Water (150 mL) was added and the whole was extracted with ethyl acetate (200 mL). After drying over anhydrous sodium sulfate, concentration and recrystallization (heptane and dichloromethane) gave the desired product (3.25 g, 53%). M.p. 147–149° C.

Example 7

Synthesis of Methyl Ester of 6-[3-(3,5-Dimethyl-1-adamantyl)-4-methoxyphenyl]-2-naphthoic Acid 121 mg ((0.54 mmoles) of the ester obtained in Example 3 and 147.5 mg (0.505 mmoles) of the methyl ester of 6-(4-methoxyphenyl)naphthoic acid were dissolved in a mixture of 0.4 mL cyclohexane and 1 mL of 1,2-dichloroethane. While stirring vigorously, concentrated sulfuric acid (15 microliters, 0.27 mmoles) was added. The mixture was heated to 75° C. for 5 hours while stirring and stirred at 25° C. for 28 days. The solvent was removed in vacuo, and the material purified by column chromatography on silica using toluene as an eluant, yielding 157 mg (68%) of the desired product. M.p.=143–147° C.

Example 8

Synthesis of Methyl Ester of 6-[3-(3-Methyl-1-adamantyl)-4-methoxyphenyl]-2-naphthoic Acid 36.4 mg (0.175 mmoles) of the ester obtained in Example 2 and 51 mg (0.175 mmoles) of the methyl ester of 6-(4-methoxyphenyl)naphthoic acid are dissolved in a mixture of 0.14 mL cyclohexane and 0.35 mL of 1,2-dichloroethane. While stirring vigorously, concentrated sulfuric acid (5 microliters, 0.09 mmoles) is added. The mixture is stirred at 90° C. for 14 hours and at 25° C. for 24 hours. The solvent is removed in vacuo, and the material is purified by column chromatography on silica using toluene as an eluant, yielding 15.8 mg (20.5%) of the desired product. M.p.=146–147° C.

Example 9

Synthesis of Methyl Ester of 6-[3-(2-Oxa-1-adamantyl)-4-methoxyphenyl]-2-naphthoic Acid 142 mg (0.61 moles) of 2-oxa-1-adamantyl mesylate (from Example 4) and 137.5 mg (0.47 mmoles) of the methyl ester of 6-(4-methoxyphenyl)naphthoic acid are dissolved in 2 mL of dichloromethane and 0.2 mL of cyclohexane. 80 microliters (0.9 mmoles) of concentrated trifluorosulfonic acid are added. The mixture is stirred for 90 hours, dissolved in 25 mL dichloromethane, filtered, and adsorbed onto 2 grams of silica. The compound is purified by column chromatography on silica using toluene as an eluant, yielding 32.3 mg (16%) of the desired product. TLC: Rf=0.12 (silica plate: eluant=toluene).

$^1$HNMR (CDCl$_3$, 500 MHz): 1.709 (d, 2H J=12.3 Hz); 1.817 (d, 2H J=12.3 Hz); 1.92652 (d, 1H J=12.7 Hz); 1.996 (d, 1H J=12.5 Hz); 2.099 (d, 2H J=12.2 Hz); 2.217 (s, 2H); 2.706 (d, 2H J=12.7 Hz); 3.886 (s, 3H); 3.986 (s, 3H); 4.379 (s, 1H); 6.988 (d, 1H, J=8.4 Hz); 7.577 (dd, 1H, J1=8.4 Hz, J2=2.2 Hz); 7.849 (d, 1H, J=7.8 Hz); 7.919 (d, 1H, J=8.7 Hz); 7.971 (d, 1H, J=8.7 Hz); 8.054 (dd, 1H, J1=11.1 Hz, J2=1.6 Hz); 8.076 (s, 1H); 8.079 (s, 1H); 8.600 (s, 1H).

Example 10

Synthesis of Methyl Ester of 6-[3-(2-Oxa-3-methyl-1-adamantyl)4-methoxyphenyl]-2-naphthoic Acid 76.2 mg (0.26 mmoles) of the methyl ester of 6-(4-methoxyphenyl)naphthoic acid and 61.3 mg (0.25 mmoles) of the mesylate obtained in Example 5 are suspended in a mixture of 0.85 mL 1,2-dichloroethane and 80 microliters of cyclohexane. 30 microliters of concentrated trifluorosulfonic acid (0.339 mmoles) is added, and the suspension is stirred at 25° C. for 5 days. The product is purified using preparative TLC on silica places with toluene as the eluant, yielding 4.5 mg (4%) of the desired product. TLC: Rf=0.38 (silica plate: eluant=toluene). $^1$HNMR (DMSO-d6, 500 Mhz) 1.763 (s, 4H), 2.074 (s, 3H), 2.140 (s, 5H), 2.539 (s, 3H), 3.872 (s, 3H), 3.924 (s, 3H), 7,128 (d, 1H, J=3.5 Hz), 7.584 (d, 1H, J=1.8 Hz), 7.664 (dd, 1H, J1=1.7 Hz), J2=8.7 Hz), 7.914 (dd, 1H, J1=1.5 Hz, J2=7.3 Hz), 7.988 (d, 1H, J=9.1 Hz), 8.108 (d, 1H, J=9.1 Hz), 8.185 (d, 1H, J=3.6 Hz), 3.238 (s, 1H), 8.637 (s, 1H). MS 454 (M$^+$).

Example 11

Synthesis of Methyl Ester of 6-[3-(3,5-Dimethyl-1-adamantyl)-4,5-methylenedioxyphenyl]-2-naphthoic Acid To a mixture of methyl ester of 6-(3,4-methylenedioxyphenyl)-2-naphthoic acid (see Example 6, 70 mg, 0.23 mmole), 3,5-dimethyl-1-adamantyl acetate (see Example 3, 63.4 mg, 0.285 mmole) in dichloroethane (1.2 mL) were added two drops of cyclohexane followed by addition of trifluoromethanesulfonic acid (0.030 mL, 0.34 mmole). The reaction mixture was stirred at room temperature for four days. Preparative TLC purification (10% ethyl acetate in hexanes) gave the desired product (44 mg, 40%.). Rf: 0.24 (10% ethyl acetate/hexane). $^1$HNMR (CDCl$_3$, 500 Mhz) 0.899 (s, 6H), 1.233 (s, 2H), 1.395 (d, 2H, J=13.3 Hz), 1.463 (d, 2H, J=12.2 Hz), 1.681 (d, 2H, J=12.2 Hz), 1.741 (d, 2H, J=12.1 Hz), 1.929 (d, 2H, J=1.4 Hz), 2.18–2.20 (m, 1H), 3.990 (s, 3H), 6.012 (s, 2H), 7.078 (d, 1H, J=1.7 Hz), 7.099 (s, 1H), 7.743 (dd, 1H, J1=1.7 Hz, J2=3.5 Hz), 7.919 (d, 1H, J=8.7 Hz), 7.974 (s, 1H), 7.983 (d, 1H, J=9.2 Hz), 8.072 (d, 1H, J=7.8 Hz), 8.610 (s, 1H). MS 468 (M$^+$).

Example 12

Synthesis of Methyl Ester of 6-[3-(3-Methyl-1-adamantyl)-4,5-methylenedioxyphenyl]-2-naphthoic Acid To a mixture of methyl ester of 6-(3,4-methylenedioxyphenyl)-2-naphthoic acid (see Example 6, 48.9 mg, 0.16 mmole), 3-methyl-1-adamantyl acetate (see Example 2, 40.2 mg, 0.193 mmole) in dichloroethane (1.2 mL) were added two drops of cyclohexane followed by the addition of trifluoromethanesulfonic acid (0.020 mL, 0.227 mmole). The reaction mixture was stirred at room temperature for four days. Preparative TLC purification (10% ethyl acetate in hexanes) gave the desired product (35 mg, 48%). Rf=0.27 (10% ethyl acetate in hexanes). $^1$HNMR (CDCl$_3$, 500 Mhz), 0.87 (s. 3H), 1.520 (s, 4H), 1.661 (d, 1H, J=12.5 Hz), 1.737 (d, 1H, J=12.4 Hz), 1.787 (s, 2H), 1.984 (d, 2H, J=11.7 Hz), 2.049 (d, 2H, J=12.1 Hz), 2.154 (s, 2H), 3.990 (s, 3H), 6.012 (s, 2H), 7.084 (s, 1H), 7.105 (s, 1H), 7.745 (d, 1H, J=8.3 Hz), 7.914 (d, 1H, J=8.6 Hz), 7.974 (s, 1H), 7.982 (d, 1H, J=8.4 Hz), 8.071 (d, 1H, J=3.6 Hz), 8.610 (s, 1H). MS 454 (M$^+$).

Example 13

Synthesis of Methyl Ester of 6-[3-1(2-Oxa-1-adamantyl)-4,5-methylenedioxyphenyl]-2-naphthoic Acid To a mixture of methyl ester of 6-(3,4-methylenedioxyphenyl)-2-naphthoic acid (see Example 6, 22.6 mg, 0.074 mmole), 2-oxa-1-adamantyl mesylate (see Example 4, 50 mg, 0.22 mmole) in dichloroethane (1.2 mL) were added two drops of cyclohexane followed by the addition of trifluoromethanesulfonic acid (0.020 mL, 0.227 mmole). The reaction mixture was stirred at room temperature for two days. Preparative TLC purification (10% ethyl acetate in hexanes) gave the desired product (5 mg, 15%). Rf=0.15 (silica 10% ethyl acetate, 90% hexanes). MS: 443 (M+H$^+$).

Example 14

Synthesis of 6-[3-(3-Methyl-1-adamantyl)-4-methoxyphenyl]-2-naphthoic Acid 10 mg (0.0226 mmoles) of the ester from Example 8 are dissolved in 0.5 mL of n-butanol and treated with 0.1 mL of 1 molar potassium hydroxide in n-BuOH (0.1 mmoles of potassium hydroxide). The solution is heated at 105° C. for 110 minutes and cooled to 25° C. The reaction mixture is treated with 2.5 mL of water and 0.5 mL of acetic acid, and the volatiles are removed under vacuum. Washing with water to remove potassium acetate and drying under vacuum yields 6.6 mg (68.5%) of the desired product. $^1$HNMR (DMSO-d6, 500 Mhz) 0.873 (s, 3H), 1.203 (s, 2H), 1.363 (d, 2H, J=11.9 Hz), 1.434 (d, 2H, J=11.3 Hz), 1.723 (d, 2H, J=12.0 Hz), 1.783 (d, 2H, J=11.9 Hz), 1.968 (s, 2H), 2.154 (s, 2H), 3.862 (s, 3H), 7.124 (d, 1H, J=3.7 Hz), 7.566 (d, 1H, J=2.2 Hz), 7.653 (dd, 1H, J1=1.8 Hz, J2=8.0 Hz), 7.88 (d, 1H, J1=1.4 Hz, J2=8.7 Hz), 7.987 (dd, 1H, J1=1.5 Hz, J2=8.8 Hz), 8.078 (d, 1H, J=8.6 Hz), 8.162 (d, 1H, 1=8.6 Hz), 8.199 (s, 1H), 8.599 (s, 1H).

Example 15

Synthesis of 6-[3-(3,5-Dimethyl-1-adamantyl)-4-methoxyphenyl]-2-naphthoic Acid

The ester from example 7 is hydrolyzed as described in Example 14, yielding 35% of the desired product. M.p. 258–263° C.

Example 16

Synthesis of 6-[3-(2-Oxa-1-adamantyl)-4-methoxyphenyl]-2-naphthoic Acid

The ester from Example 9 is hydrolyzed as described in Example 14, yielding 70% of the desired product. $^1$HNMR (DMSO-d6, 500 MHz), 1.632 (s, 2H), 1.696 (s, 2H, J=11.8 Hz), 1.910 (s, 2H), 1.969 (d, 2H, J=11.6 Hz), 2.167 (s, 2H), 2.686 (s, 2H), 3.856 (s, 3H), 4.330 (s, 1H), 7.130 (d, 1H, J=8.6 Hz), 7.678 (dd, 1H, J1=7.3 Hz, J2=2.0 Hz), 7.827 (d, 1H, J=8.7 Hz), 7.975 (d, 1H, J=2.4 Hz), 7.984 (s, 1H), 8.0686 (d, 1H, J=8.5 Hz), 8.138 (d, 1H, J=8.7 Hz), 8.147 (s, 1H), 8.562 (s, 1H).

Example 17

Synthesis of 6-[3-(2-Oxa-3-methyl-1-adamantyl)-4-methoxyphenyl]-2-naphthoic Acid The ester from Example 10 is hydrolyzed as described in Example 14, yielding the desired product. $^1$HNMR (DMSO-d6, 500 MHz), 1.763 (s, 4H), 2.073 (s, 3H), 2.141 (s, 5H), 2.539 (s, 3H), 3.871 (s, 3H), 7.126 (d, 1H, J=7.6 Hz), 7.580 (d, 11H, J=1.8 Hz), 7.659 (dd, 1H, J1=8.1 Hz, J2=1.7 Hz), 7.895 (d, 1H, J=9.3 Hz), 7.974 (dd, 1H, J1=8.8, J2=1.4), 8.077 (d, 1H, J=8.7 Hz), 3.156 (d, 1H, J=8.6 Hz), 8.223 (s, 1H), 8.587 (s, 1H).

Example 18

Synthesis of 6-[3-(3,5-Dimethyl-1-adamantyl)-4,5-methylenedioxyphenyl]-2-naphthoic Acid The ester from Example 11 is hydrolyzed as described in Example 14, yielding 78% of the desired product. Rf: 0.23 (50% ethyl acetate in hexanes). $^1$HNMR (DMSO-d6, 500 Mhz), 0.875 (s, 6H), 1.208 (s, 2H), 1.368 (d, 2H, J=11.5 Hz), 1.432 (d, 2H, J=12.0 Hz), 1.674 (d, 2H, J=12.0 Hz), 1.717 (d, 2H, J=12.0 Hz), 1.905 (s, 2H), 2.16–2.18 (m, 1H), 6.063 (s, 2H), 7.143 (s, 1H), 7.284 (s, 1H), 7.843 (d, 1H, J=8.5 Hz), 7.990 (d, 1H, J=9.0 Hz), 8.024 (d, 1H, J=9.0 Hz), 8.120 (d, 1H, J=8.5 Hz), 8.186 (s, 1H), 8.561 (s, 1H). MS 454 (M$^+$).

Example 19

Synthesis of 6-[3-(3-Methyl-1-adamantyl)-4,5-methylenedioxyphenyl]-2-naphthoic Acid The ester from Example 12 is hydrolyzed as described in Example 14, yielding 59% of the desired product. Rf: 0.22 (50% ethyl acetate in hexanes). $^1$HNMR (DMSO-d6, 500 Mhz): 0.861 (s, 3H), 1.485 (s, 4H), 1.622 (d, 1H, J=12.4 Hz), 1.692 (d, 1H, J=12.3 Hz), 1.766 (s, 2H), 1.962 (d, 2H, J=11.5 Hz), 2.009 (d, 2H, J=12.3 Hz), 2.117 (s, 2H), 6.065 (s, 2H), 7.156 (s, 1H), 7.297 (s, 1H), 7.877 (d, 1H, J=8.3 Hz), 7.981 (d, 1H, J=8.2 Hz), 8.060 (d, 1H, J=8.6 Hz), 8.147 (d, 1H, J=3.6 Hz), 8.221 (s, 1H), 8.601 (s, 1H). MS: 440 (M$^+$).

Example 20

Synthesis of 6-[3-1(2-Oxa-1-adamantyl)-4,5-methylenedioxyphenyl]-2-naphthoic Acid The ester from Example 13 is hydrolyzed as described in Example 14, yielding 65% of the desired product. Rf: 0.16 (50% ethyl acetate in hexanes).

Example 21

Preparation of the Methyl Ester of 6-[3-(3-Methyl-1-adamantyl)-4-hydroxyphenyl]-2-naphthalenecarboxylic Acid To a solution of the ester obtained in Example 8 (129 mg, 0.29 mmol) in anhydrous methylene chloride (5 mL) was added to 2M boron tribromide solution (2.1 mL, 2.1 mmol) slowly under argon at 0° C. The solution was stirred at 0° C. for 90 minutes before adding methanol (20 mL). After 16 hours, the reaction solution was poured into aqueous solution of sodium hydrogen sulfate (0.48 g) and potassium carbonate (0.8 g). The mixture was extracted with ether (2×100 mL). The ether layer was dried over sodium sulfate and evaporated. Column chromatography with silica gel gave the desired product (83 mg, 65.6%), $^1$NMR (CDCL$_3$ 500 MHz); 0.891 (s, 3H), 1.528 (s, 4H), 1.665 (d, 1H, J=12.4), 1.754 (d, 1H, J=12.0), 1.892 (s, 2H), 2.087 (d, 2H, J=11.2 Hz), 2.155 (d, 2H, J=11.1 Hz), 2.167 (s, 2H), 3.99 (s, 3H), 6.780 (d, 1H, J=8.2), 7.430 (dd, 1H, J=2.0, 8.2), 7.585 (d, 1H, J=2.0), 7.774 (dd, 1H, J=1.4, 8.4), 7.918 (d, 1H, J=8.6), 7.988 (d, 1H, J=8.2), 7.996 (s, 1H), 8,069 (dd, 1H, J=1.6, 8.4), 8.612 (s,1H).

Example 22

Preparation of 6-[3-(3-Methyl-1-adamantyl)-4-hydroxyphenyl]-2-naphthalene-carboxylic Acid A solution of the ester from Example 24 (75 mg. 0.172 mmol) in 0.25 M potassium hydroxide in n-butanol (10 mL) was refluxed under argon for 4 hours. A slightly excess of acetic acid was added and the whole was extracted with methylene chloride. The organic layer was washed with brine, dried over sodium sulfate and evaporated. Column chromatography with silica gel (1:15 methanol/methylene chloride) gave the desired product in almost quantitative yield. $^1$NMR(DMSO-d$_6$, 500 MHz): 0.843 (s, 3H), 1.464 (s, 4H), 1.6109 (d, III), 1.668 (d, 1H), 1.844 (s, 2H), 2.06 (m, 6H), 6.91 (d, 1H, T=8.0 Hz), 7.49 (dd, 1H, J=2.5, 10.4), 7.85 (dd, 1H, J=1.5, 8.8), 7.96 (dd, 1H, J=0.6–7.6), 8.05 (d, 1H, J=8.7), 8.124 (d, 1H, J=8.7), 8.147 (s, 1H), 8.571 (s, 1H).

Example 23

Preparation of N-(2-Aminoethyl){-6-[3-(1-adamantyl)-4-methoxyphenyl]-2-naphthalenecarboxamide}

To a suspension of 6-[3-(1-adamantyl)-4-methoxyphenyl]-2-naphthalenecarboxylic acid (3 g, 7.27 mmoles) in dry toluene (20 mL) was added thionyl chloride (0.6 mL, 8.22 mmoles) and DMF (0.04 mL) under argon. The reaction mixture was heated to 100° C. for ten minutes and another 0.04 mL of DMF was added. After 30 minutes, more thionyl chloride (0.1 mL, 1.37 mmoles) was added and the reaction mixture was heated to 110° C. for 60 minutes. The solvent and excess thionyl chloride were removed in vacuo. The resulting solid was stirred with 100 mL dry methylene chloride under argon. This was added to a mixture of ethylene diamine (5.25 mL, 70 mmoles) in dry methylene chloride under argon at 0° C. while stirring rapidly. The solution was allowed to warm to ambient temperature while stirring rapidly during one hour. The reaction mixture was poured carefully into 350 mL of 1N aqueous HCl while stirring, and the methylene chloride was removed in vacuo. The resulting precipitate (hydrochloride salt of the product) was washed with 1N HCl, water, THF, and methylene chloride. Yield of hydrochloride salt: 2.76 g, 77%. The free base was generated by neutralizing with aqueous sodium bicarbonate and extracting the product into tetrahydrofuran, drying the organic layer over sodium sulfate, and removing the solvent. MS 455 (M+H$^+$).

Example 24

Preparation of N-{6-[3-(1-Adamantyl)-4-methoxyphenyl]-2-naphthalene-carboxoyl}homopiperazide This amide was prepared from 6-[3-(1-adamantyl)-4-methoxyphenyl]-2-naphthalenecarboxylic acid and homopiperazine using a procedure analogous to the one in Example 24. MS: 495 (M+H$^+$).

Example 25

Preparation of N-{6-[3-(1-Adamantyl)-4,5-methylenedioxyl-2-naphthalene-carboxoyl}piperazide This amide was prepared from 6-[3-(1-adamantyl)-4,5-methylenedioxy]-2-naphthalenecarboxylic acid and piperazine using a procedure analogous to the one in Example 24. MS: 495 (M+H$^+$).

Example 26

N-{6-[3-(1-Adamantyl)-4,5-methylenedioxy]-2-naphthalenecarboxoyl}homopiperazide This amide was prepared from 6-[3-(1-adamantyl)-4,5-methylenedioxy]-2-naphthalenecarboxylic acid and homopiperazine using a procedure analogous to the one in Example 24. MS: 509 (M+H$^+$).

Example 27

N-(2-Aminoethyl){-6-[3-(1-adamantyl)-4,5-methylenedioxyphenyl]-2-naphthalenecarboxamide}

This amide was prepared from 6-[3-(1-adamantyl)-4,5-methylenedioxy]-2-naphthalenecarboxylic acid and ethylenediamine using a procedure analogous to the one in Example 24. MS: 469 (M+H$^+$).

Example 28

N-(2-Dimethylaminoethyl)-{6-[3-(1-adamantyl)-4,5-methylenedioxypehnyl]-2-naphthalenecarboxamide}

This amide was prepared from 6-[3-(1-adamantyl)-4,5-methylenedioxy]-2-naphthalenecarboxylic acid and 2-dimethylaminoethylamine using a procedure analogous to the one in Example 24. MS: 495 (M-H$^-$).

Example 29

The anti-cancer activity of various adamantyl retinoid compounds according to the invention was compared to all-trans-retinoic acid using cell-based high throughput screening assays. Specifically, the following compounds were tested in such assays: all-trans-retinoic acid, 6[3(1-adamantyl)-4-methoxyphenyl]-2-naphthoic acid, 2-[3-(1-adamantyl)-4-methoxyphenyl]-5-benzimidazole carboxylic acid, 6-[3-(1-adamantyl)-4-hydroxy-5-methoxyphenyl]-2-naphthoic acid, 6-[3-(1-adamantyl)-4-acetoxymethylphenyl]-2-naphthoic acid and 6-[3-(1-adamantyl)-4,5-methylenedioxyphenyl]-2-naphthoic acid.

These compounds were tested against a panel of human tumor cell lines having a variety of tissue origins, and having distinct tumor characteristics. The tumor cell cultures were exposed to the above retinoid compounds for a specific duration. After such exposure, the percentage of surviving cells was then measured using standard assays. These results were then compared for different compounds, with an active compound being defined as one which results in a percentage survival of less than 80.

These results are contained in FIG. 1. Based on these results, it can be seen that compounds according to the invention were active against a number of distinct human cancers. By contrast, all-trans-retinoic acid did not give comparable results.

Example 30

Figure 3A:
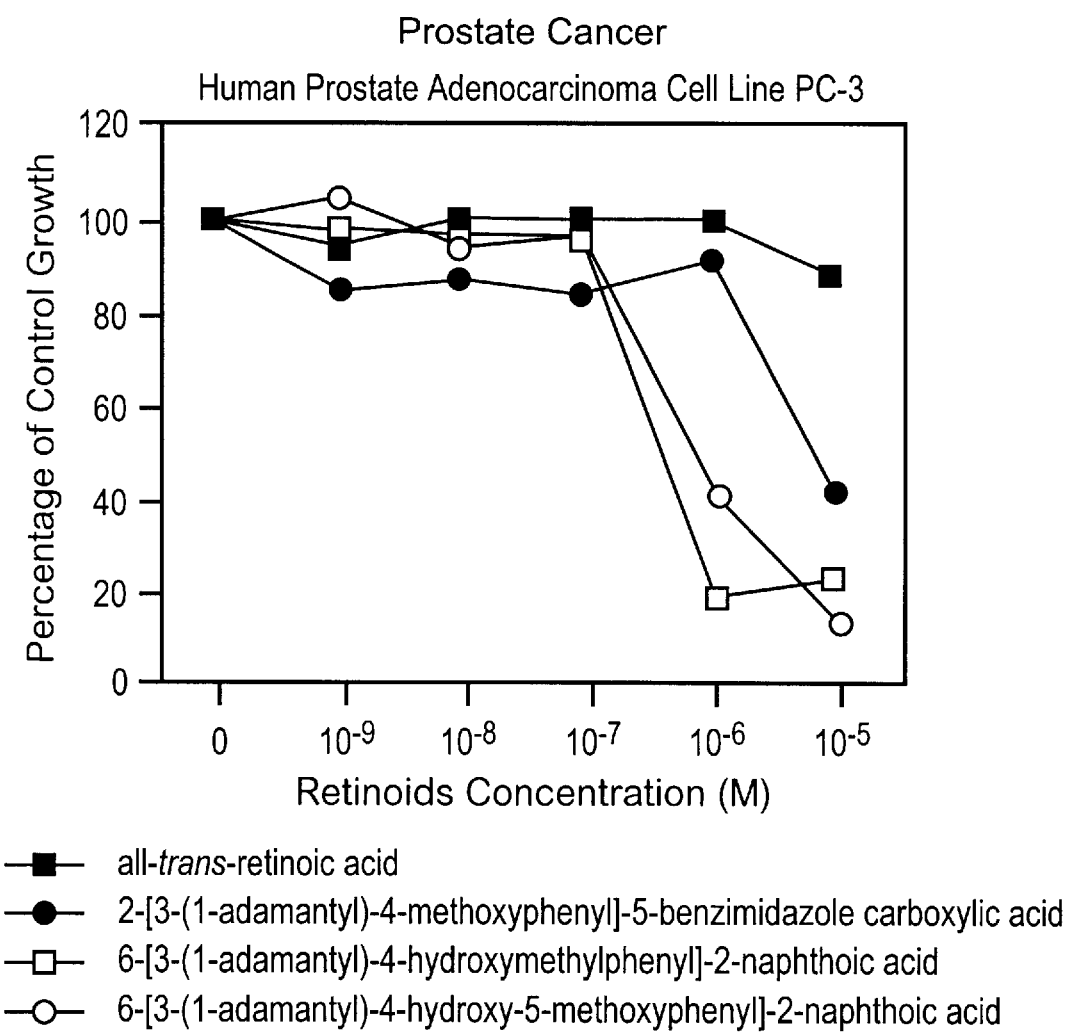
FIG. 3 compares the activity of selected adamantyl retinoids according to the invention and all-trans-retinoic acid against human prostate adenocarcinoma, human metastatic prostate adenocarcinoma, and human prostate carcinoma cell lines.
Figure 3B:
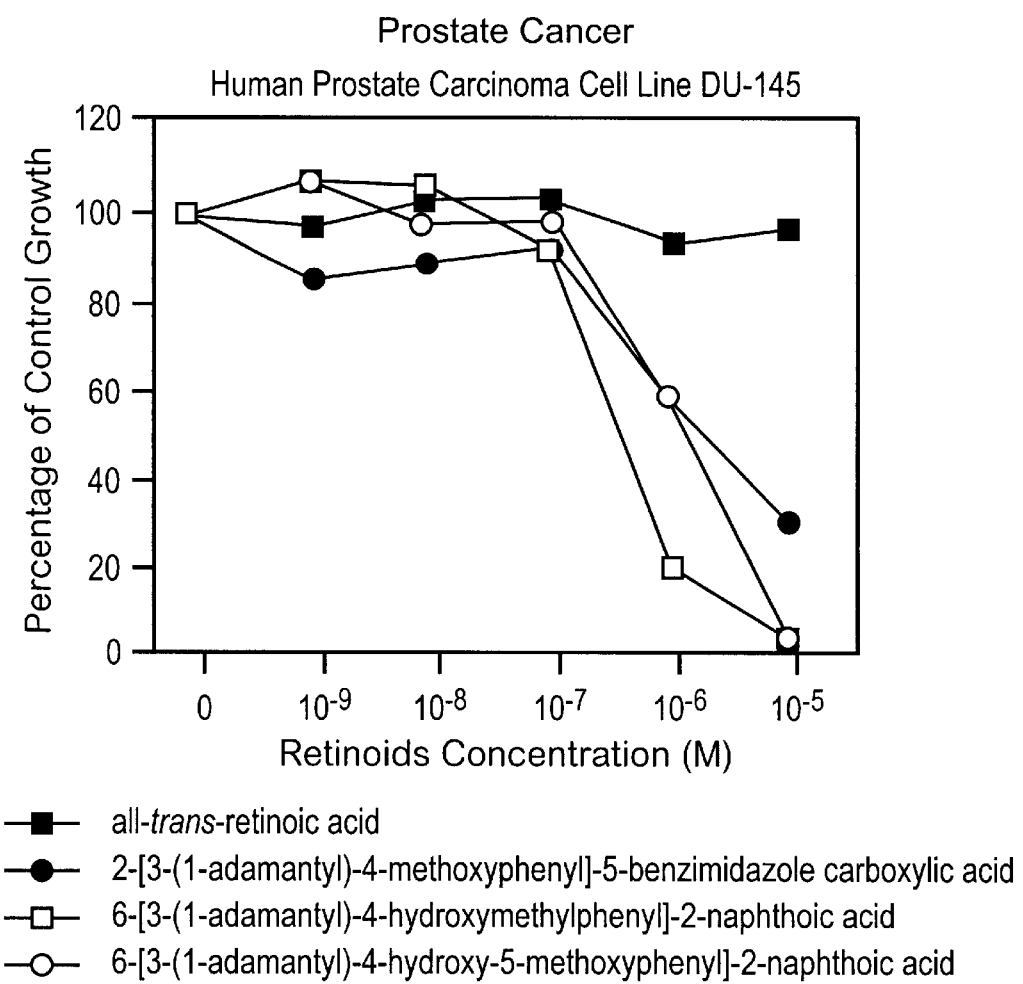
Figure 3C:
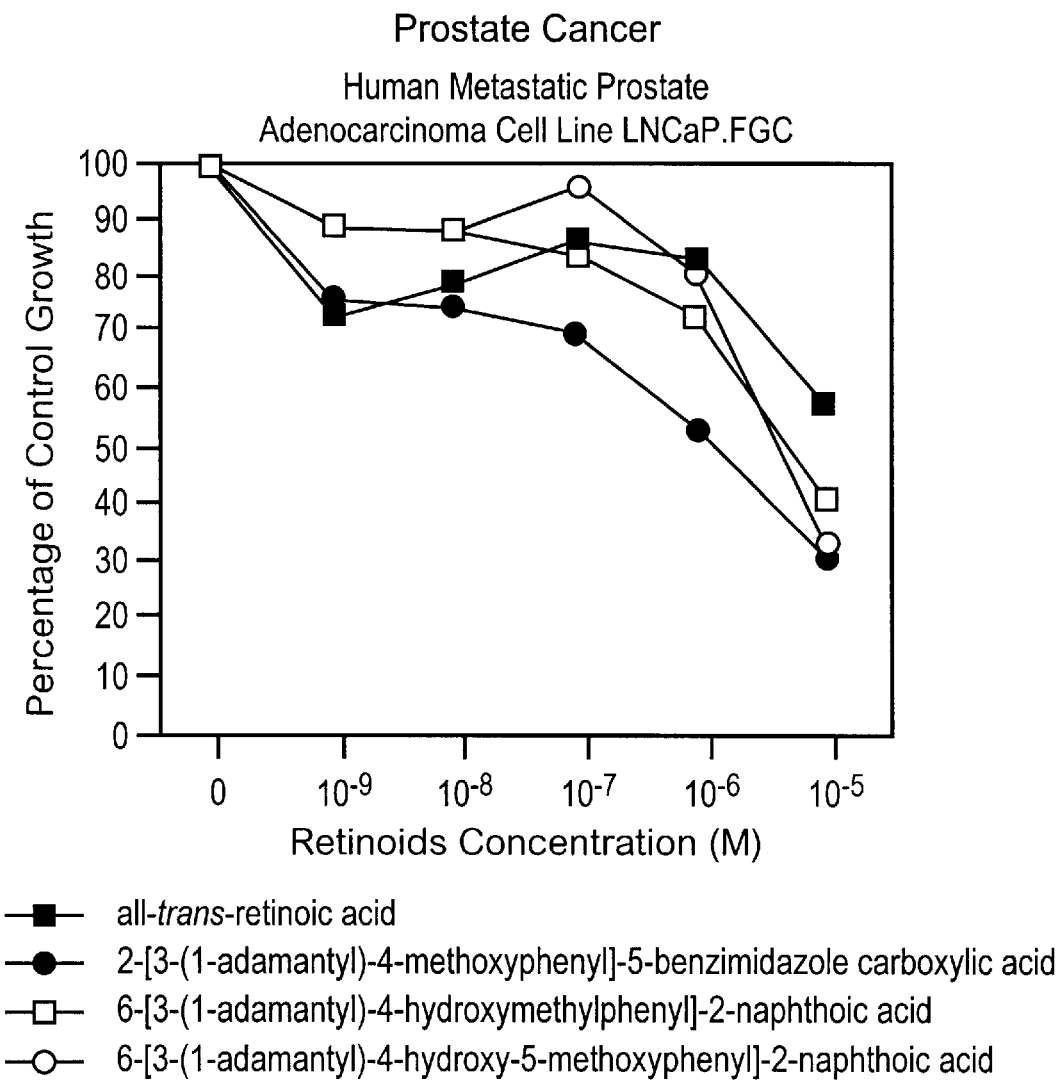
Figure 4:
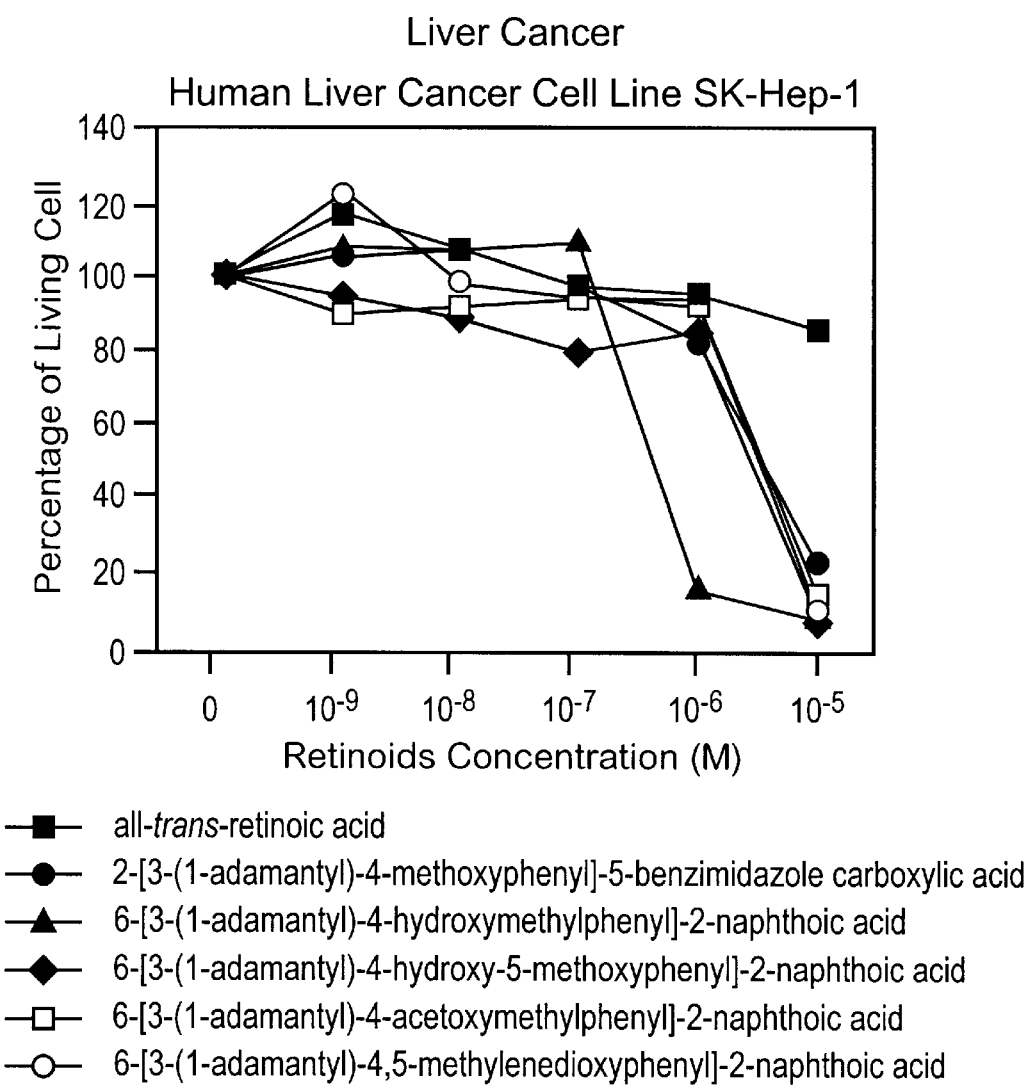
FIG. 4 compares the activity of selected adamantyl retinoids according to the invention and all-trans-retinoic acid against a human liver cancer cell line.

Based on the previous results, various active compounds according to the invention, in particular 2-[3-(1-adamantyl)-4-methoxyphenyl]-5-benzimidazole carboxylic acid, 6-[3-(1-adamantyl)-4-hydroxymethylphenyl]-2-naphthoic acid; 6-[3-(1-adamantyl)-4-hydroxy-5-methoxyphenyl]-2-naphthoic acid; 6-[3-(1-adamantyl)-4,5-methylenedioxyphenyl]-2-naphthoic acid, as well as all-trans-retinoic acid, were tested against various human cancer cell lines at retinoid concentrations ranging from 10$^{-9}$ M to 10$^{-5}$ M. These results are contained in FIGS. 2–4, and show that adamantyl compounds according to the invention exhibit significant anti-cancer activity. By contrast, all-trans-retinoic acid did not exhibit similar activity.

Example 31

The anti cancer activity of a compound according to the invention, 6-[3-(1-adamantyl)-4,5-methylenedioxyphenyl]-2-naphthoic acid was also evaluated in a human xenograft mouse animal model containing human pancreatic cancer BxPC-3 tumor cells. Starting twenty-eight days after inoculation of tumor cells, said xenograft containing mice were administered the retinoid compound intraperitoneally at a dosage of 80 mg/kg body weight. Also, a control group of said mice was inoculated under similar conditions with the pharmaceutical vehicle used for formulation (but lacking the retinoid compound).

Figure 5:
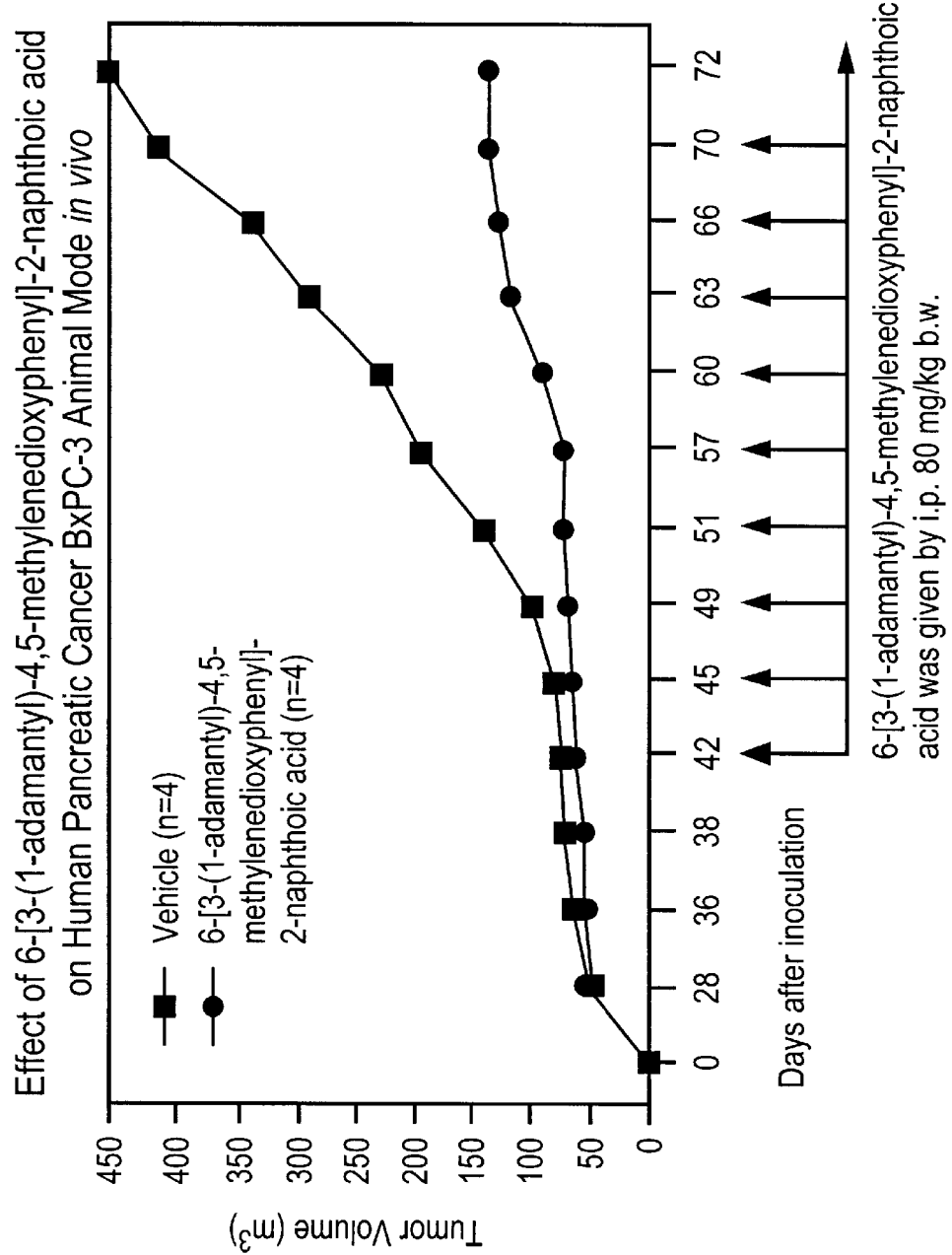
FIG. 5 shows the effect of 6-[3-(1-adamantyl)-4,5-methylenedioxyphenyl]-2-naphthoic acid in a human pancreatic cancer BxP-3 animal model.
Figure 6A:
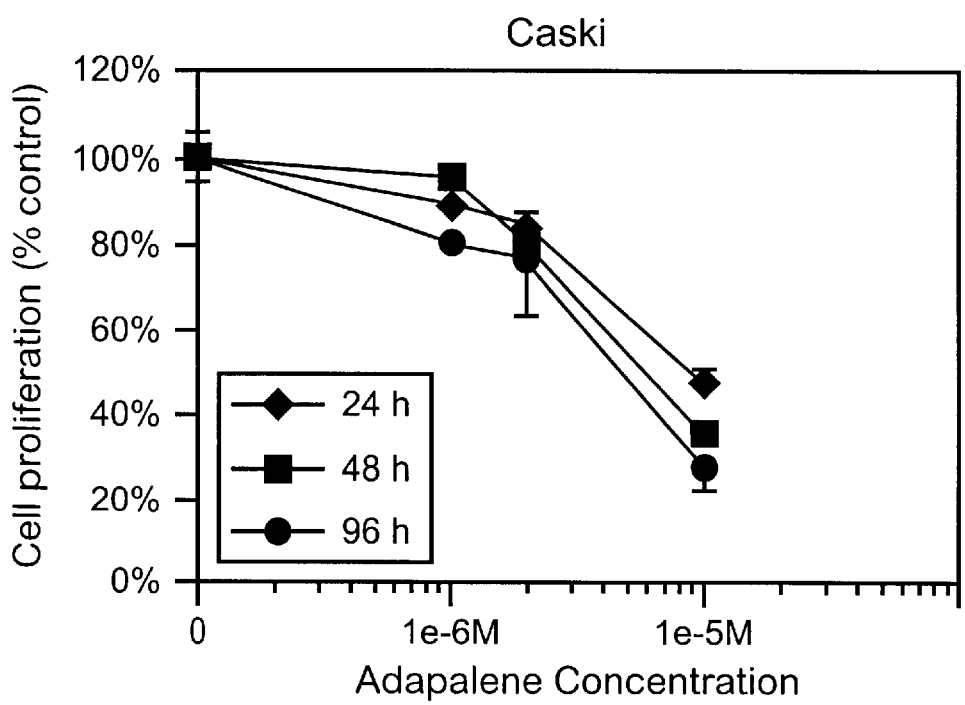
FIG. 6 compares the effect of 6-[3-(1-adamantyl)-4-methoxyphenyl]-2-naphthoic acid, and all trans retinoic acid (tRA) on the proliferation of cervical cancer cell lines.
Figure 6B:
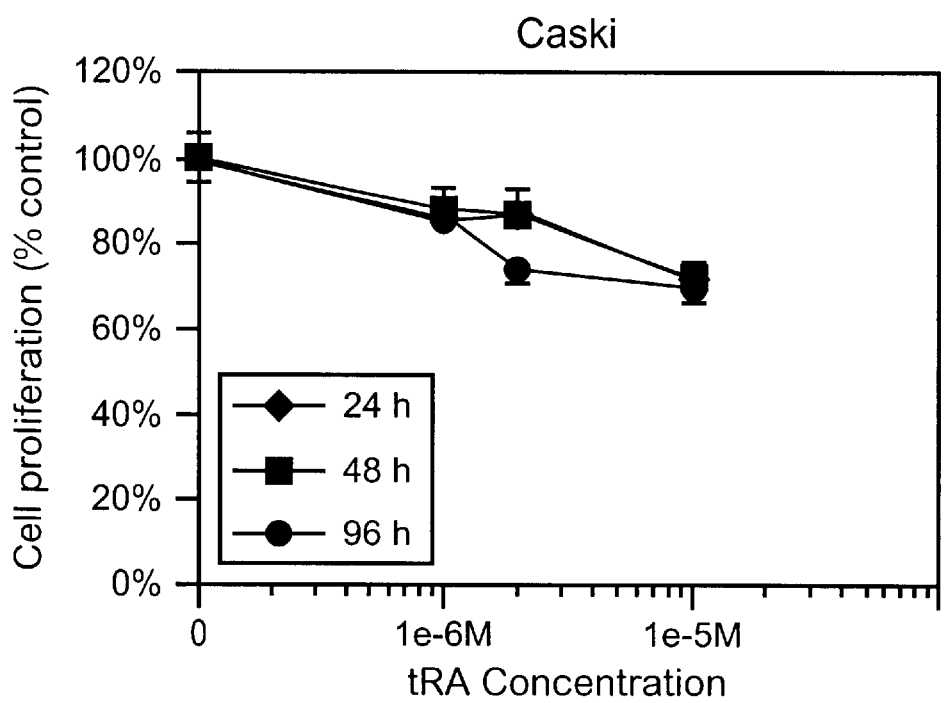
Figure 6C:
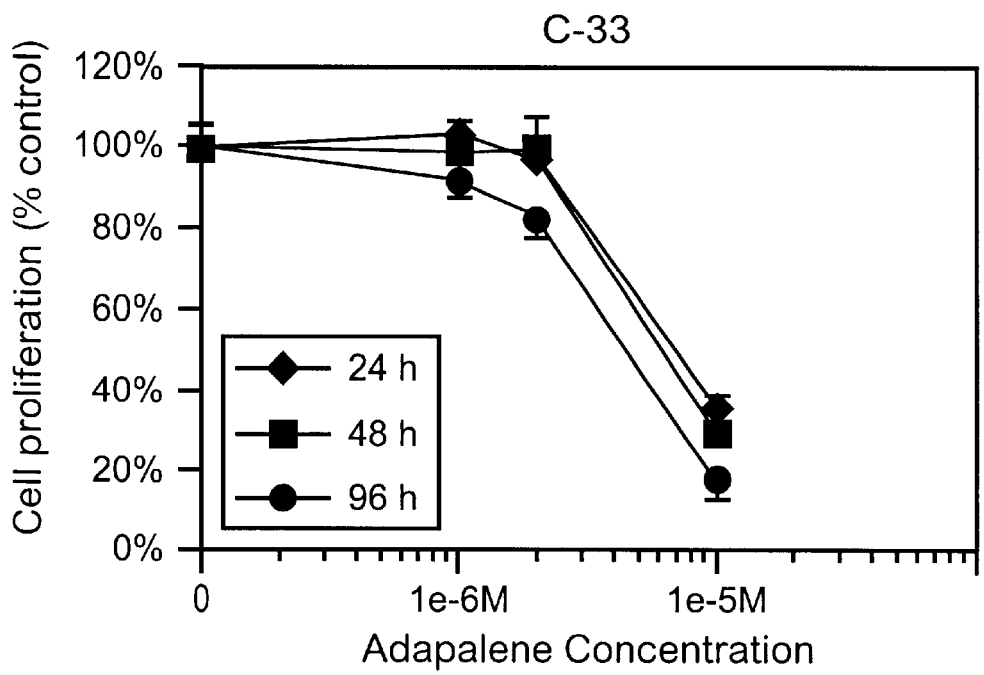
Figure 6D:
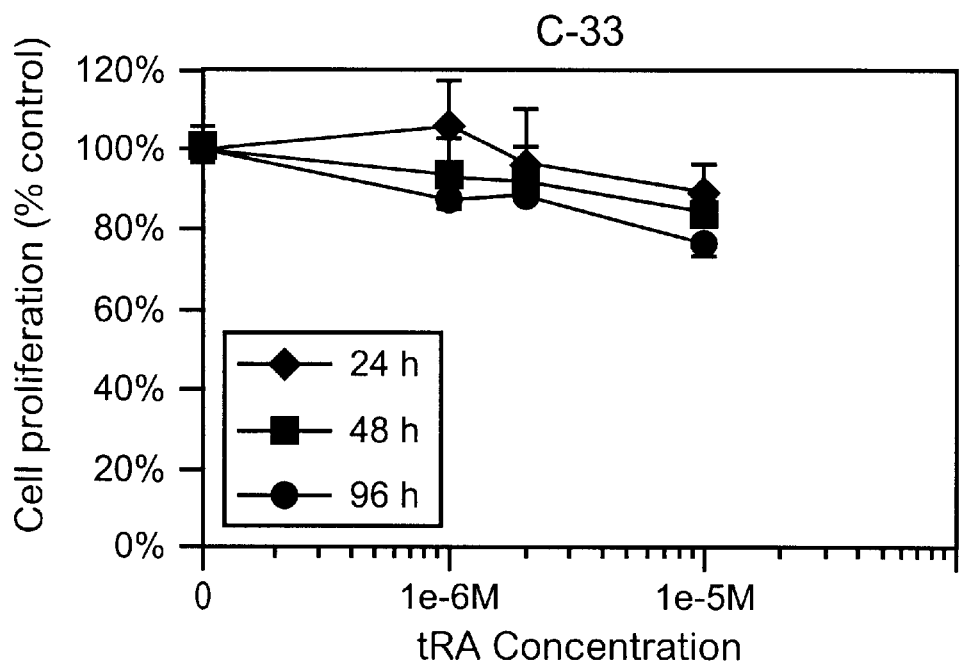

These results are contained in FIG. 5 and show that the retinoid compound according to the invention, 6-[3-(1-adamantyl)-4,5-methylenedioxyphenyl]-2-naphthoic acid resulted in substantial reduction in tumor size compared to the control group which were not administered this retinoid compound. Therefore, based on these results, it is apparent that the anti-cancer activity of adamantyl compounds according to the invention, which is apparently attributable to apoptosis inducing activity, is observed both in vitro and in vivo.

Example 32

Effect of 6-[3-(1-adamantyl)-4-methoxyphenyl]-2-naphthoic Acid ("Adapalene") on Proliferation of Cervical Cancer Cell Lines Adapalene was shown to inhibit the proliferation of cervical cancer cell lines in a dose-dependent manner. Two human cervical cancer cell lines, the Caski and C33A (which contains integrated human papillomavirus sequences) were treated with adapalene at concentrations of 1, 2 and 10 $\mu$M for 24, 48 and 96 hours or with tretinoin as a control. Afterward, human cervical cancer cells, which had been treated for 28 or 48 hours, were then washed and incubated in a medium lacking adapalene.

After a total incubation time of 96 hours, a proliferation assay was performed to assess the extent of inhibition of proliferation or cell killing. As can be seen from the results contained in FIG. 6, maximum inhibition of cell proliferation occurred at 10 $\mu$M adapalene. The EC$_{50}$ (concentration of adapalene that provides for 50% inhibition of cell proliferation) for the tested human cervical cancer cell lines was estimated to be approximately 5 $\mu$M. Under the in vitro conditions of this experiment, incubation longer than 24 hours apparently had only a marginal effect on proliferation, as the increase in inhibition of cell growth between 48 and 96 hours was not found to be statistically significant (p>0.05). These results provide evidence that a compound according to the invention, adapalene, effectively inhibits the proliferation of human cervical cancer cells.

Example 33

Figure 7A:
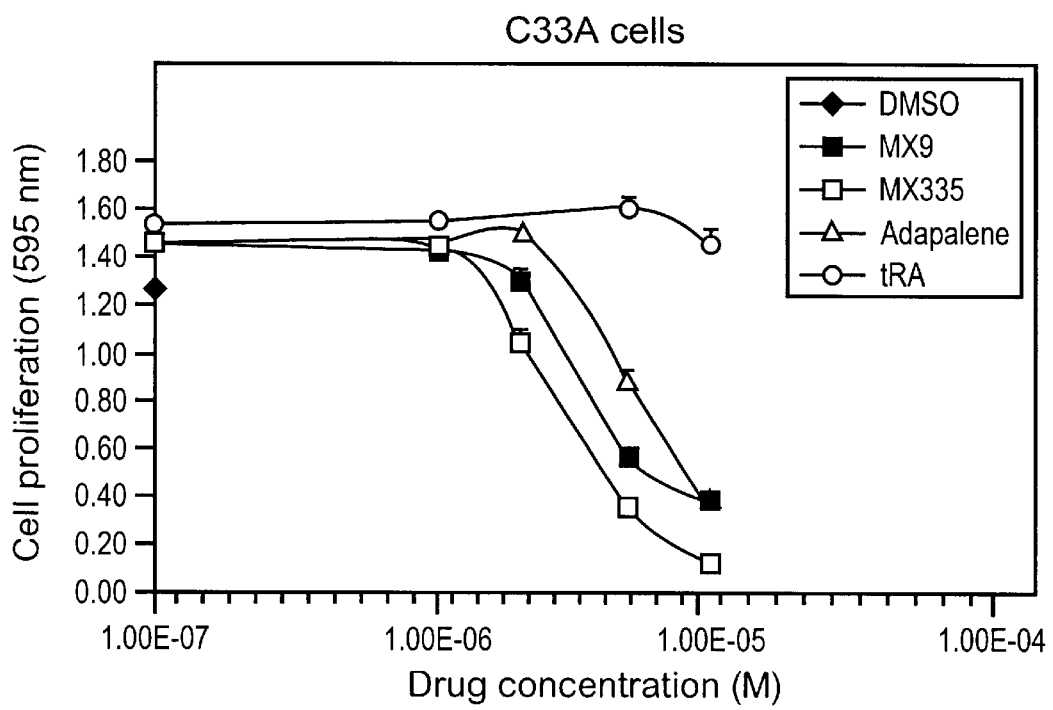
FIG. 7 shows the effect of the compounds according to the invention on proliferation of two cervical cancer cell lines.
Figure 7B:
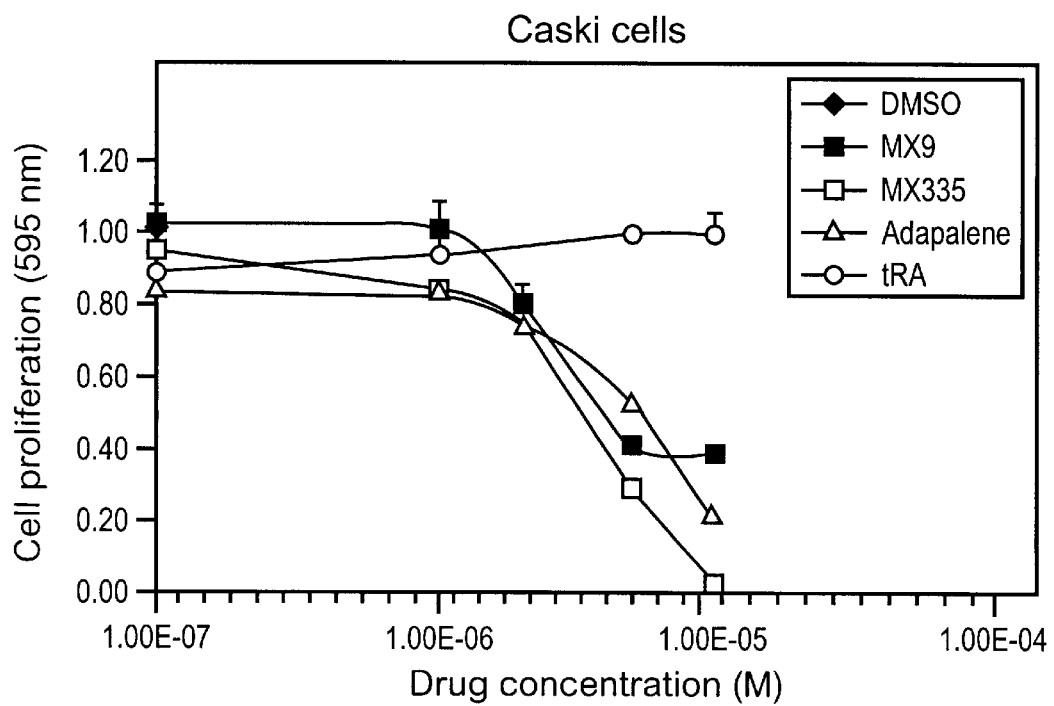

Another experiment was also conducted to compare the effect of three different retinoid compounds according to the invention, i.e., 6-[3-(1-adamantyl)-4-methoxyphenyl]-2-naphthoic acid, 2-[3-(1-adamantyl)-4-methoxyphenyl]-5-benzimidazole carboxylic acid, and 6-[3-(1-adamantyl)-4,5-methylenedioxyphenyl]-2-naphthoic acid, a control (DMSO), and a control retinoid (all-trans retinoic acid) on the proliferation of several human cervical cancer cell lines (C33A cells and Caski cells). As shown in FIG. 7, the three retinoid compounds according to the invention had a strong inhibitory effect on the proliferation of said human cervical cell lines. By contrast, the control retinoid (all-trans-retinoic acid) had no significant effect on cell proliferation.

Example 34

Figure 8:
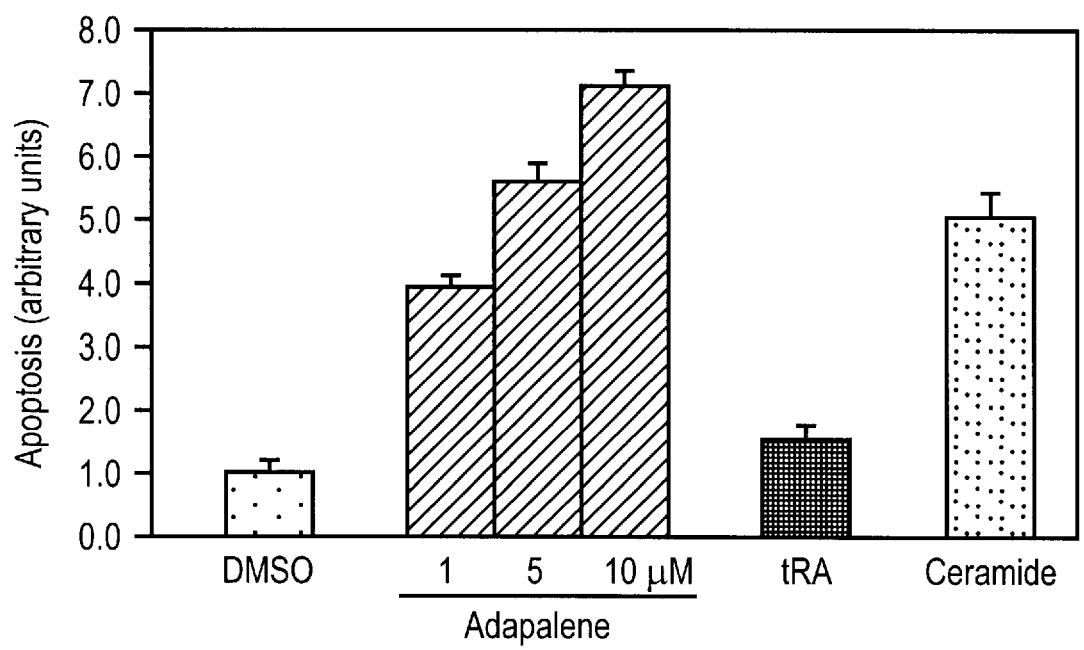
FIG. 8 compares the effect of 6-[3-(1-adamantyl)-4-methoxyphenyl]-2-naphthoic acid, CD437, ceramide, and all trans retinoic acid on apoptosis of cervical cancer cell lines.

Apoptotic Effect of 6-[3-(1-Adamantyl)-4-methoxyphenyl]-2-naphthoic Acid ("Adapalene") on Cervical Cancer Cell Lines An experiment was conducted to determine whether the compounds of the previous example could not only inhibit the growth of cervical cancer cells, but also eliminate such cells by inducing programmed cell death ("apoptosis"). It was found that these compounds did induce apoptosis. In particular, adapalene was shown to effectively inhibit the proliferation of cervical cancer cells by inducing apoptosis. In this experiment cells were labeled with BrdU for six hours. After labeling, cells were treated with vehicle (DM50), or with 10 $\mu$M tRA, 0.5 mM ceramide or doses of adapalene of 1, 5 and 10 $\mu$M for eighteen hours. Apoptosis was measured using a cellular DNA fragmentation ELISA kit (available from Boehringer). These results are contained in FIG. 8. Therein, one unit represents the value obtained from cells grown in the presence of vehicle alone. As can be seen from these results, the extent of apoptosis in cells incubated with adapalene was comparable to that of cells incubated with ceramide, a potent inducer of apoptosis. By contrast, all-trans retinoic acid (tRA) did not induce apoptosis significantly. Ceramide, which was used as a positive control, also effectively induced apoptosis. These results provide further evidence that retinoid compounds according to the invention eliminate cancer cells such as cervical cancer cells by induction of apoptosis.

Example 35

Phase I/II Study: Clinical Experience with 6-[3-(1-Adamantyl)-4-methoxyphenyl]-2-naphthoic acid (Adapalene) in Patients with Cervical Intraepithelial Neoplasia Level II or III Cervical intraepithelial neoplasia (CIN) can be graded into levels I, II, and III. Level I corresponds to mild cervical dysplasia, II to moderate dysplasia, and III to severe dysplasia, and carcinoma in situ.

A clinical study was designed and approved where an aqueous adapalene gel was delivered with a cervical cap and a collagen sponge in patients with advanced cervical dysplasia (CIN II and CIN III). Inclusion criteria for enrollment included a biopsy proving diagnosis of CIN II or CIN III. Forty-nine patients received the drug and completed the study.

Two patients that received only a four day treatment showed no response. Among the forty-seven remaining evaluable patients that received either an eight day or fourteen day treatment, the overall response rate (partial plus complete) at ninety days after treatment was 48.7% (23/47). Twelve patients showed complete and eleven partial responses Twenty-six patients showed stable disease with no progression. A partial response was a response where the disease regressed to CIN I, a condition that is characterized by a high spontaneous regression rate and which does not require surgical intervention.

As shown in Table II, response rates did not increase with increased length of treatment from eight to fourteen days. The highest overall response rate was observed in patients treated for eight days at 60.8%.

Also, Tables III–VI contain further information relating to the patients treated, and their responses. Specifically, Table III below contains information relating to the demographics and dosing of evaluable patients.

Table IV below tabulates patient response (complete, partial, overall, stable or progression) based on length of treatment.

Table V below compares patient response as a function of length of treatment and severity of dysplasia.

Table VI below compares patient response based on severity of dysplasia and smoking status.

As can be seen from the results tabulated in the following Tables, all averse effects reported were mild, with no patient being withdrawn from the study because of an adverse event. Moreover, all patients who initiated the treatment were able to complete the treatment regimen. These results indicate that non-surgical therapy using a retinoid such as adapalene in a collagen sponge/cervical cap delivery system is a viable alternative to destructive treatment for women with high grade cervical dysplasia. Moreover, since low grade cervical dysplasia is also present in patients with high grade diseases, such treatment is also suitable for treating low grade disease.

TABLE II

MX6: Phase I–II Study Results

| Treatment Results | CIN II N = 27 | CIN III N = 21 | Total N = 48 |
| --- | --- | --- | --- |
| CIN Resolved | 30% | 24% | 27% |
| Improved to CIN I | 22% | 19% | 21% |
| Overall "cure" | 52% | 43% | 48% |
| Improved from CIN III to CIN II | — | 29% | 13% |
| Overall Response | 52% | 72% | 61% |

TABLE III

Demographics and Dosing of Evaluable Patients

| | | Number of Patients (%) Length of Treatment in Days | | |
| --- | --- | --- | --- | --- |
| | All Patients | 4 | 8 | 14 |
| Number Treated | 49 | 2(3.8) | 23(46.9) | 24(49.0) |
| Age in Years | | | | |
| Range | 17–44 | 22–33 | 18–44 | 17–34 |
| Mean | 25 | 28 | 27 | 23 |
| Smoking Status | | | | |
| Smokers | 30(61.2) | 1(50.0) | 11(47.6) | 18(75.0) |
| Mean Pack-Years | 8.8 | 12.0 | 7.8 | 9.2 |
| Marital Status | | | | |
| Married | 24(49.0) | 2(100.0) | 12(52.2) | 10(41.7) |
| Race | | | | |
| White | 45(91.8) | 2(100.0) | 22(95.6) | 21(87.5) |
| Black | 1(2.0) | 0(0.0) | 0(0.0) | 1(4.2) |
| Hispanic | 1(2.0) | 0(0.0) | 1(4.3) | 0(0.0) |
| Native American | 1(2.0) | 0(0.0) | 0(0.0) | 1(4.2) |
| Mixed | 1(2.0) | 0(0.0) | 0(0.0) | 1(4.2) |
| Diagnosis | | | | |
| CIN II* | 26(53.1) | 0(0.0) | 12(52.2) | 14(58.3) |
| CIN III/CIS# | 23(46.9) | 2(100.00) | 11(47.8) | 10(41.7) |

*Cervical Intraepithelial Neoplasia Level II
Cervical Intraepithelial Neoplasia Level III/Carcinoma-in-Situ

TABLE IV

Response Based on Length of Treatment

| | Length of Treatment in Days | | |
|---|---|---|---|
| Response | 4(n = 2) | 8(n = 23) | 14(n = 24) |
| Complete | 0(0.0) | 7(30.4) | 5(20.8) |
| Partial | 0(0.0) | 7(30.4) | 4(16.7) |
| Overall | 0(0.0) | 14(60.8) | 9(37.5) |
| Stable | 2(100.0) | 9(39.1) | 15(62.5) |
| progression | 0(0.0) | 0(0.0) | 0(0.0) |

TABLE V

Response Based on Length of Treatment and Severity of Dysplasia

| | Length of Treatment in Days | | | | | |
|---|---|---|---|---|---|---|
| | 4 | | 8 | | 14 | |
| | Level of Dysplasia | | | | | |
| Response | CIN II* (n = 0) | CIN III/CIS# (n = 2) | CIN II (n = 12) | CIN III/CIS (n = 11) | CIN II (n = 14) | CIN III/CIS (n = 10) |
| Complete | 0(0.0) | 0(0.0) | 4(33.3) | 3(27.3) | 3(21.4) | 2(20.0) |
| Partial | 0(0.0) | 0(0.0) | 4(33.3) | 3(27.3) | 3(21.4) | 1(10.0) |
| Overall | 0(0.0) | 0(0.0) | 8(66.7) | 6(54.5) | 6(42.9) | 3(30.0) |
| Stable | 0(0.0) | 2(100.0) | 4(33.3) | 5(45.4) | 8(57.1) | 7(70.0) |
| Progression | 0(0.0) | 0(0.0) | 0(0.0) | 0(0.0) | 0(0.0) | 0(0.0) |

TABLE VI

Response Based on Severity of Dysplasia and Smoking Status

| Length of Treatment/ | Number Overall Responders/Total (%) | | |
|---|---|---|---|
| Smoking Status | CIN II* | CIN III/CIS# | Combined |
| 8 days/non-smokers | 3/7(42.9) | 6/7(85.7) | 9/14(64.3) |
| 8 days/smokers | 5/5(100.0) | 0/4(0.0) | 5/9(55.5) |
| 14 days/non-smokers | 3/4(75.0) | 2/3(66.7) | 5/7(71.4) |
| 14 days/smokers | 3/10(30.0) | 1/7(14.3) | 4/17(23.5) |

*Cervical Intraepithelial Neoplasia Level II
Cervical Intraepithelial Neoplasia Level III/Carcinoma-in-situ Based on the foregoing clinical results, it can be seen that Adapalene has significant therapeutic application in the treatment or prevention of human cancers such as cervical dysplasia (CIN I, II, and III), especially based on its inhibition of cancer cell proliferation and the induction of cancer cell apoptosis.

STRUCTURES OF ACTIVE COMPOUNDS

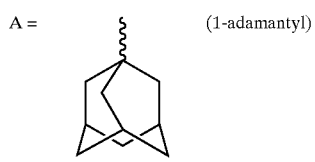

A = (1-adamantyl)

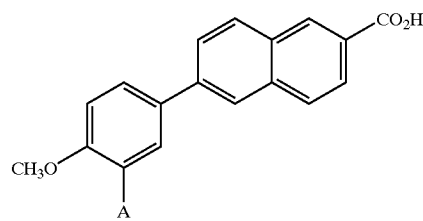

1.

-continued

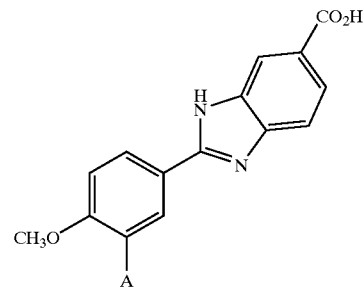

2.

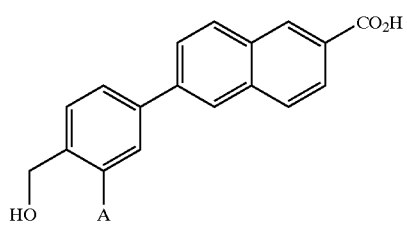

3.

4.

5. 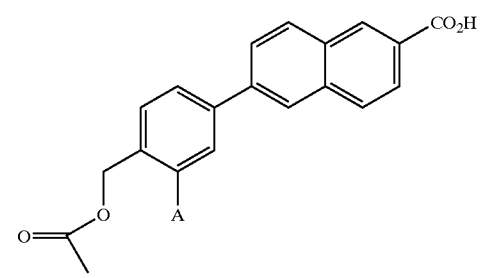
6. 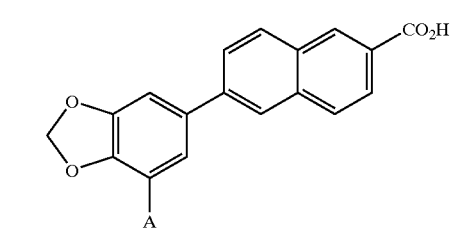
7. 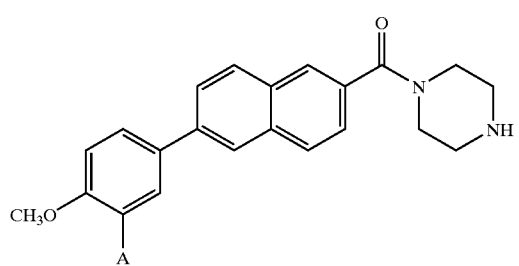
8. 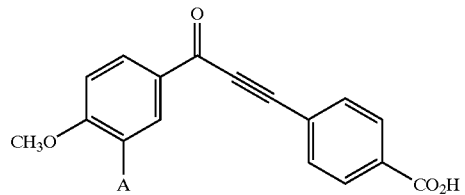
9. 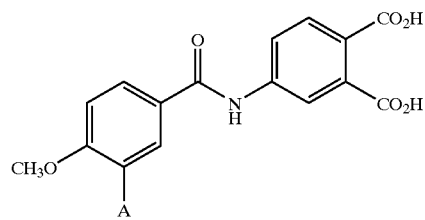
10. 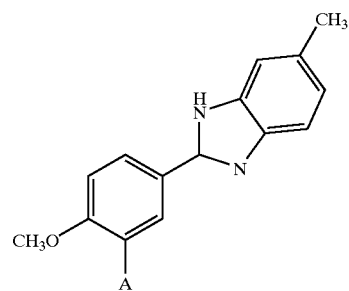
11. 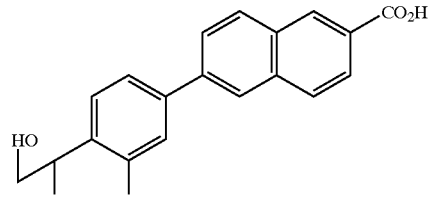
12. 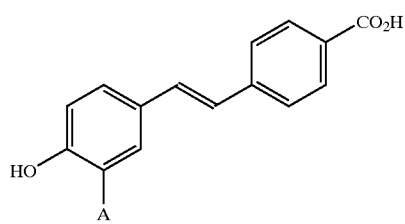
13. 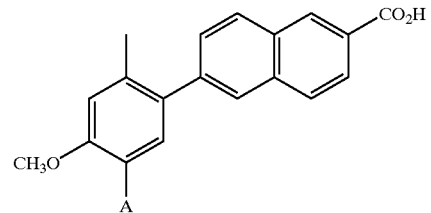
14. 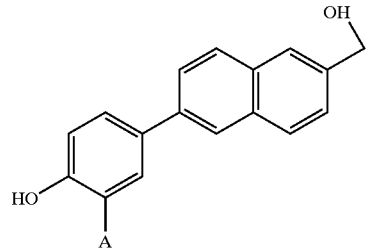
15. 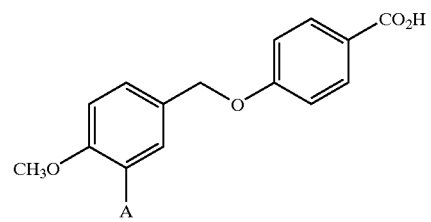
16. 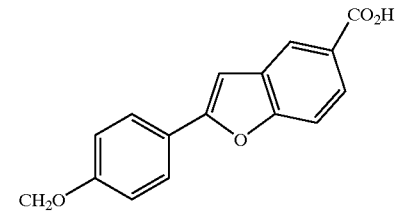
17. 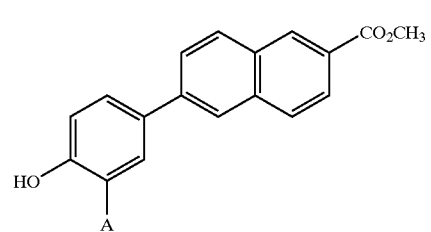

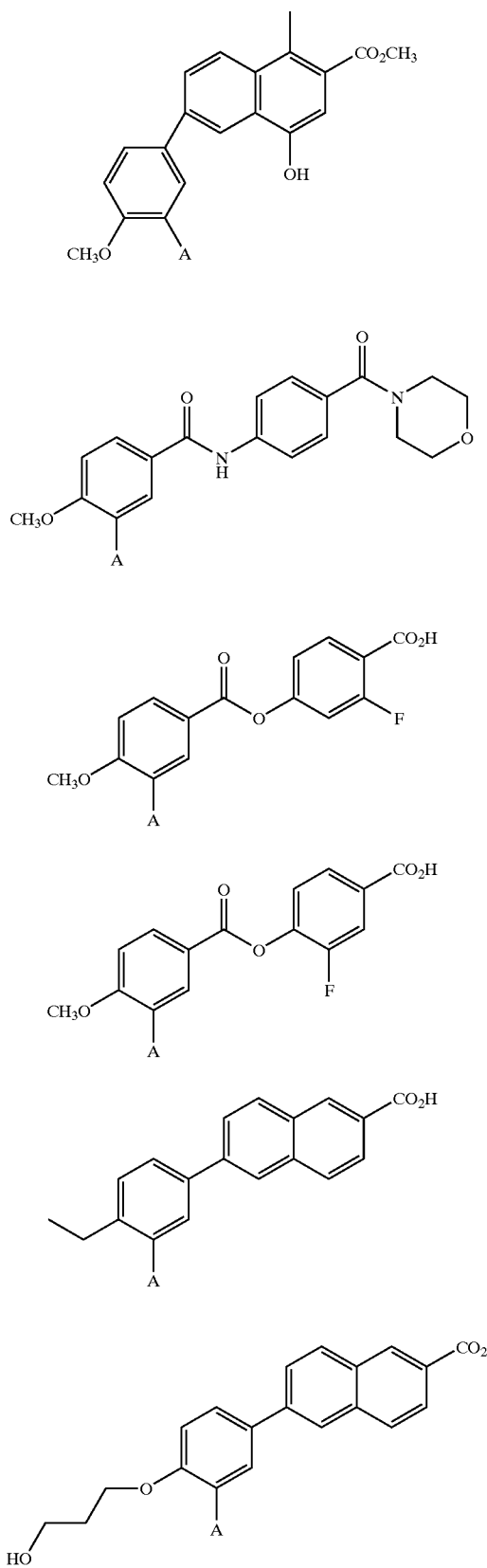
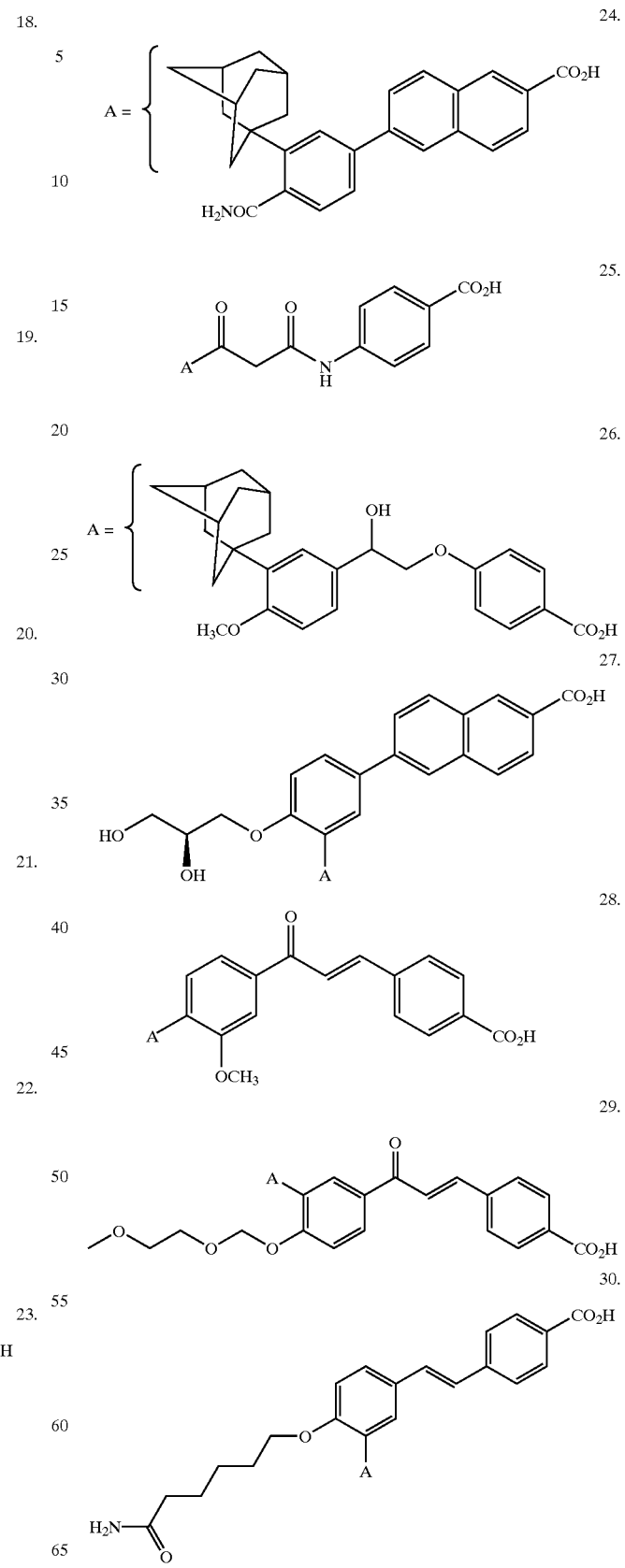

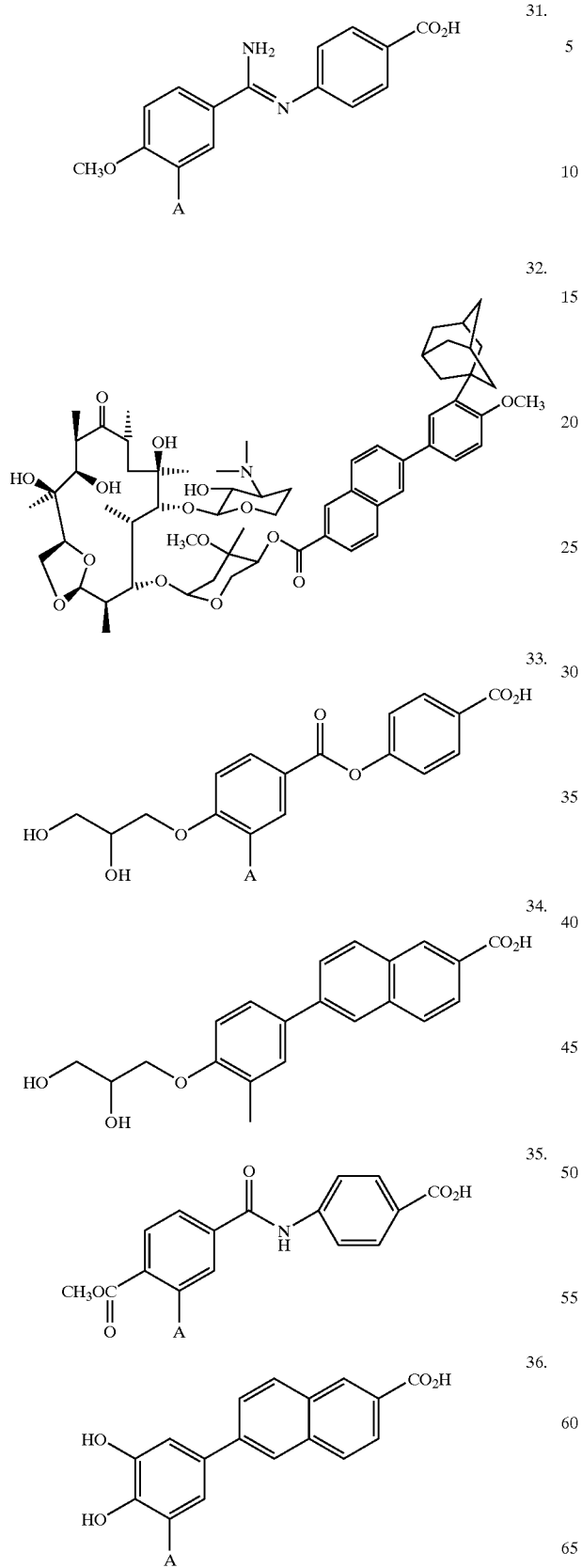
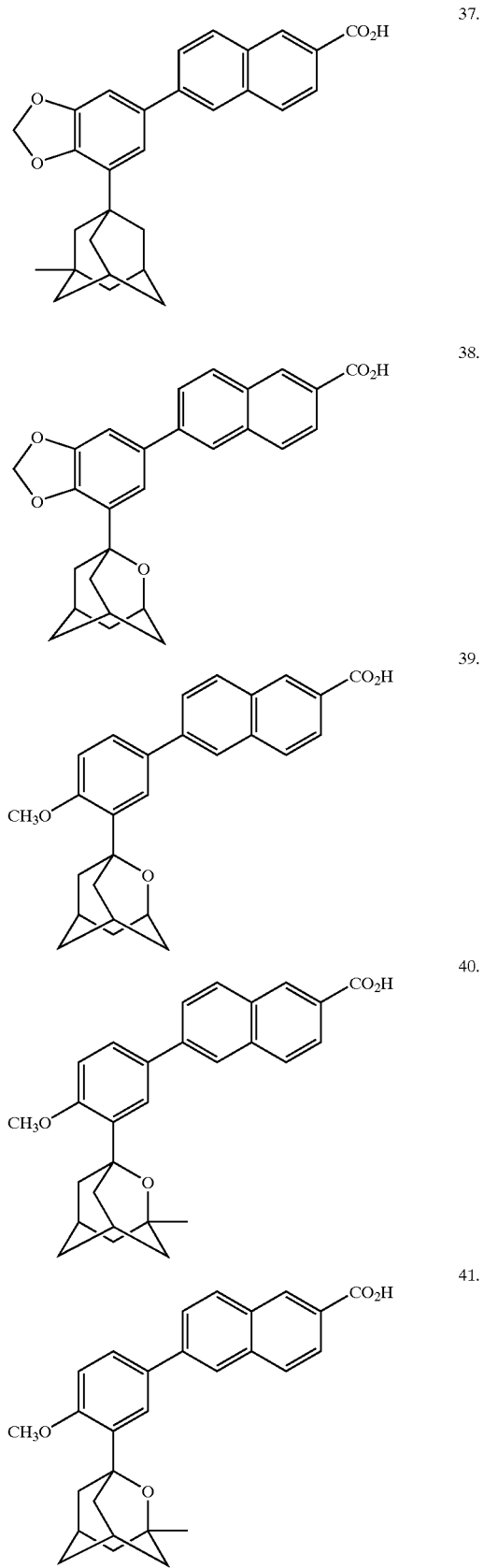

42. 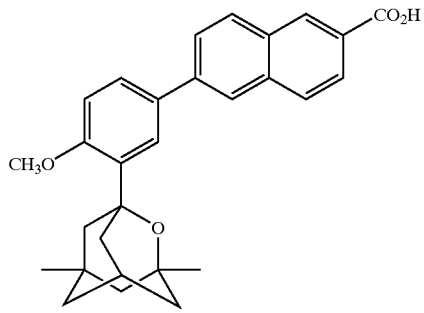

43. 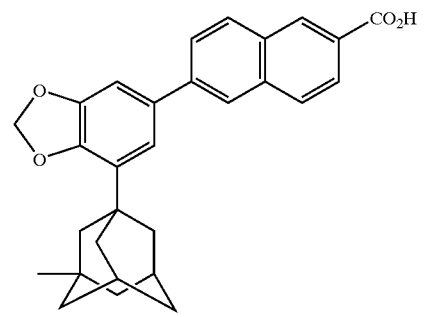

44. 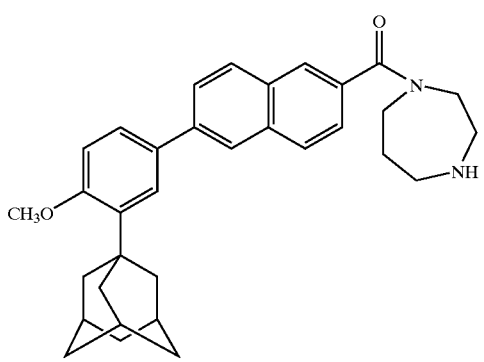

45. 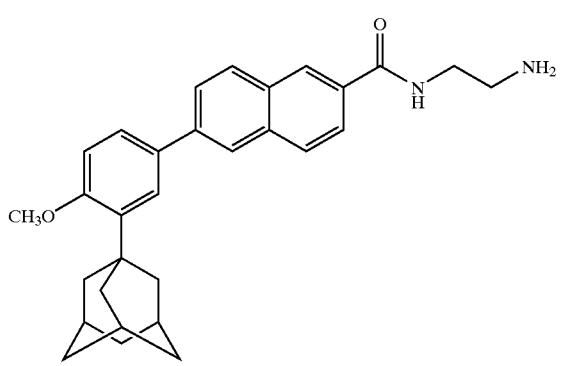

46. 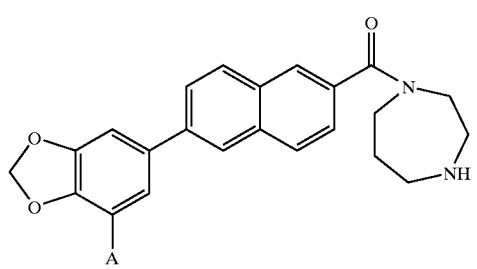

47. 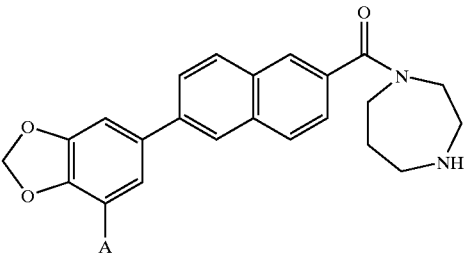

48. 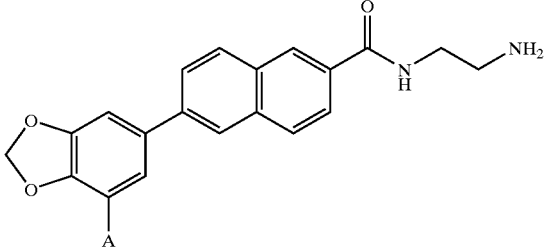

49. 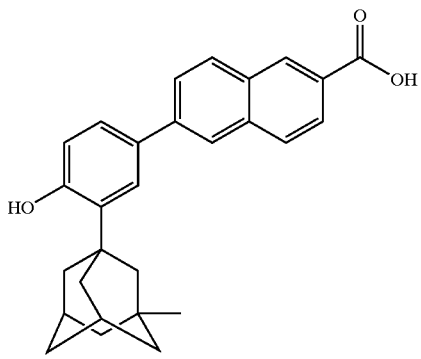

What is claimed:

1. A method for treating or preventing cancer or precancer sensitive to the formulae below in a subject in need of such treatment or prevention by inducting apoptosis of cancer or precancer cells by the administration of an apoptotic inducing effective amount of an adamantyl retinoid related compound having one of the following generic formulae set forth below or a pharmaceutically acceptable salt, optical and/or geometrical isomer thereof;

a compound of generic formula (I):

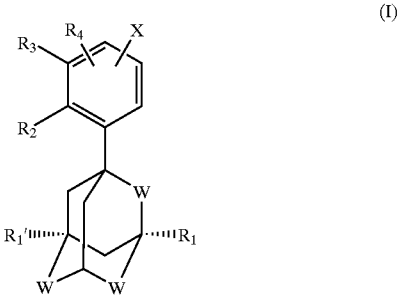

(I)

with the proviso that said retinoid of Formula (I) is not an RAR-γ receptor-specific agonist ligand, and wherein W is independently —CH$_2$—, —O—, —S—, —SO— or —SO$_2$—, X is a radical selected from among those of the following formulae (i)–(iii):

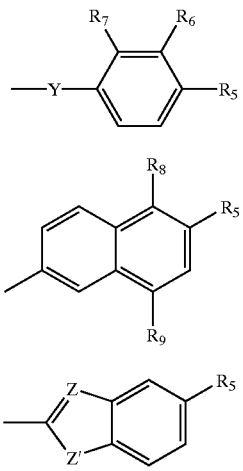

wherein
Y is a radical —CO—V—, —CH=CH—, —CH₃C=CH—, —CH=CCH₃—,

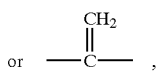

—CHOH—CH₂—O—,

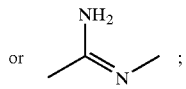

V is an oxygen atom (—O—), an aza radical (—NH—), a radical —CH=CH— or —C≡C—;
Z is a radical —CH— and Z' is an oxygen atom, or Z is a nitrogen atom (N) and Z' is an aza radical (—NH—);
$R_1$ is a hydrogen atom, halogen atom, or a lower alkyl radical;
$R'_1$ is a hydrogen atom, halogen atom, or a lower alkyl radical;
$R_2$ is a hydroxyl radical, an alkyl radical, optionally substituted by one or more hydroxyl or acyl groups, an alkoxyl radical, optionally substituted by one or more hydroxyl, alkoxyl or aminocarbonyl groups, and/or optionally interrupted by one or more oxygen atoms, an acyl radical, an aminocarbonyl radical or a halogen;
$R_3$ is a hydrogen atom, a hydroxyl radical, an alkyl radical, or an alkoxyl radical;
$R_2$ and $R_3$ can form together a radical —O—CH₂—O—;
$R_4$ is a hydrogen atom, an alkyl radical, an alkoxyl radical, or a halogen;
$R_5$ is a radical —CO—$R_{10}$, an alkyl radical, optionally substituted by one or more hydroxyl groups, or a halogen;
$R_6$ is a hydrogen atom, a halogen atom, a hydroxyl group, or an alkoxyl radical;
$R_7$ is a hydrogen atom or a halogen;
$R_8$ is a hydrogen atom, a halogen atom or an alkyl radical;
$R_9$ is a hydrogen atom, a hydroxyl radical or a halogen atom;

$R_{10}$ is a hydroxyl radical, an alkoxy radical, a radical of formula —Nr'r", wherein r' and r" represent a hydrogen atom, an optionally substituted aminoalkyl radical, a mono- or polyhydroxyalkyl radical, an optionally substituted aryl radical or an amino acid or sugar residue; or a compound having generic formula (III):

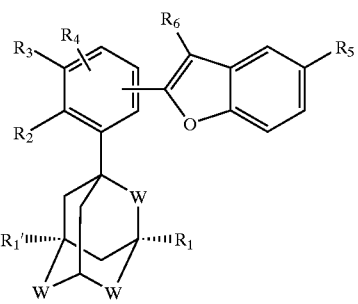

wherein $R'_1$, $R_1$, $R_2$, $R_3$, $R_4$, $R_5$, $R_6$ and W are as defined for compounds of formula (I) or is a compound of formula (IV)

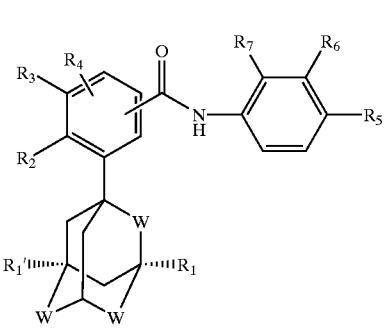

wherein $R'_1$, $R_1$, $R_2$, $R_3$, $R_4$, $R_5$, $R_6$ and W are as defined for compounds of formula (I).

2. The method of claim 1, wherein the adamantyl retinoid compound has the formula set forth below:

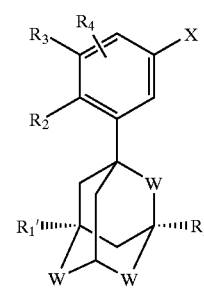

in which W, X, $R_1$, $R'_1$, $R_2$, $R_3$ and $R_4$ are as defined in claim 1, or comprises a pharmaceutically acceptable salt, or optical and/or geometrical isomer thereof, and with the proviso that said compound is not an RAR-γ receptor-specific agonist ligand.

3. The method of claim 1, wherein the adamantyl retinoid compound is that of formula (I) and at least two of $R_2$, $R_3$ and $R_4$ are not hydrogen.

4. The method of claim 2, wherein at least two of $R_2$, $R_3$ and $R_4$ are not hydrogen.

5. The method of claim 1, wherein at least two of the W radicals are —CH₂—.

6. The method of claim 5, wherein all three of the W radicals are —CH₂—.

7. The method of claim 6, wherein R'₁ and R₁ are both hydrogen.

8. The method of claim 1, wherein the adamantyl compound is of formula (III).

9. The method of claim 1, wherein the adamantyl compound is of formula (IV).

10. The method of claim 1, wherein the treated cancer is a cancer or precancer selected from the group consisting of a prostate cancer, skin cancer, pancreatic carcinoma, colon cancer, melanoma, ovarian cancer, liver cancer, small cell lung carcinoma, non-small cell lung carcinoma, cervical cancer, breast cancer, bladder cancer, brain cancer, neuroblastoma/glioblastoma, leukemia, head and neck cancer, kidney cancer, lymphoma, myeloma, and ovarian cancer.

11. The method of claim 1, wherein said method comprises administration of a compound selected from the group consisting of 6-[3-(1-adamantyl)-4-methoxyphenyl]-2-naphthoic acid; 2-[3-(1-adamantyl)-4-methoxyphenyl]-5-benzimidazole carboxylic acid; 6-[3-(1-adamantyl)-4-hydroxymethylphenyl]-2-naphthoic acid; 6-[3-(1-adamantyl)-4-hydroxy-5-methoxyphenyl]-2-naphthoic acid; 6-[3-(1-adamantyl)-4-acetoxymethylphenyl]-2-naphthoic acid; 6-[3-(1-adamantyl)-4,5-methylenedioxyphenyl]-2-naphthoic acid; N-{6-[3-(1-adamantyl)-4-methoxyphenyl]-2-naphthalenecarboxoyl}piperizide; 4-{3-oxo-3-[3-(1-adamantyl)-4-methoxyphenyl]-1-propynyl}benzoic acid; 4-[N-(3-(1-adamantyl)-4-methoxybenzoyl)amido]2-methoxybenzoic acid; 2-[3-(1-adamantyl)-4-methoxyphenyl]-5-methylbenzimidazole; 6-[3-(1-adamantyl)-4-(1,2-dihydroxyethyl)-phenyl]-2-naphthoic acid; 6-[3-(1-adamantyl)-4-hydroxy-6-methylphenyl]-2-naphthoic acid; 6-[3-(1-adamantyl)-4-methoxy-6-methylphenyl]-2-naphthoic acid; 6-[3-(1-adamantyl)-4-hydroxyphenyl]-2-hydroxymethylnaphthalene; 4-[3-(1-adamantyl)-4-methoxybenzyloxy]benzoic acid; 2-[3-(1-adamantyl)-4-methoxyphenyl]-5-benzofurancarboxylic acid; methyl ester of 6-[3-(1-adamantyl)-4-hydroxyphenyl]-2-naphthoic acid; methyl ester of 1-methyl-4-hydroxy-6-[3-(1-adamantyl)-4-methoxyphenyl]-2-naphthoic acid; N-{4-[N-(3-(1-adamantyl)-4-methoxybenzoyl)amido]benzoyl}morpholide; 4-[3-(1-adamantyl)-4-methoxybenzoyloxy]-2-fluorobenzoic acid; 4-hydroxycarbonyl-2-fluorophenyl ester of 3-(1-adamantyl)-4-methoxybenzoic acid; 6-[3-(1-adamantyl)-4-ethylphenyl]-2-naphthoic acid; 6-[3-(1-adamantyl)-4-(3-hydroxypropoxy)phenyl]-2-naphthoic acid; 6-[3-(1-adamantyl)-4-aminocarbonylphenyl]-2-naphthoic acid; N-(4-carboxyphenyl)-3-(1-adamantyl)-3-oxopropionamide; 2-hydroxy-4-{2-[3-(1-adamantyl)-4-methoxyphenyl]-2-hydroxyethoxy}benzoic acid; (S)-6-[3-(1-adamantyl)-4-(2S,3-dihydroxypropoxy)phenyl]-2-naphthoic acid; (E) 4-{3-oxo-3-[3-methoxy-4-(1-adamantyl)phenyl]prop-1-enyl}benzoic acid; (E) 4-{3-oxo-3-[4-(2-methoxyethoxymethoxy)-3-(1-adamantyl)phenyl]prop-1-enyl}benzoic acid; (E) 4-{2-[4-(6-aminocarbonylpentyloxy)-3-(1-adamantyl)phenyl]ethenyl}benzoic acid; 3-(1-adamantyl)-4-methoxy-N-(4-carboxyphenyl)benzamidine; 4"-Erythromycin A ester of 6-[3-(1-adamantyl)-4-methoxyphenyl]2-naphthoic acid; 4-carboxyphenyl ester of 3-(1-adamantyl)-4-(2,3-dihydroxyproxy)benzoic acid; 6-[3-(1-adamantyl)-4-(2,3-dihydroxypropoxy)phenyl]-2-naphthoic acid; N-4-carboxyphenyl 3-(1-adamantyl)-4-(methoxycarbonyl)benzamide; 6-[3-(1-adamantyl)-4,5-dihydroxyphenyl]-2-naphthoic acid; 6-[3-(3-methyl-1-adamantyl)-4,5-methylenedioxyphenyl]-2-naphthoic acid; 6-[3-(2-oxa-1-adamantyl)-4,5-methylenedioxyphenyl]-2-naphthoic acid; 6-[3-(2-oxa-1-adamantyl)-4-methoxyphenyl]-2-naphthoic acid; 6-[3-(2-oxa-3-methyl-1-adamantyl)-4-methoxyphenyl]-2-naphthoic acid; 6-[3-(3-methyl-1-adamantyl)-4-methoxyphenyl]-2-naphthoic acid; 6-[3-(3,5-dimethyl-1-adamantyl)-4-methoxyphenyl]-2-naphthoic acid; 6-[3-(3,5-dimethyl-1-adamantyl)-4,5-methylenedioxyphenyl]-2-naphthoic acid; N-{6-[3-(1-adamantyl)-4-methoxyphenyl]-2-naphthalenecarboxoyl}homopiperazide; N-(2-aminoethyl)-{6-[3-(1-adamantyl)-4-methoxyphenyl]-2-naphthalenecarboxamide]; N-{6-[3-(1-adamantyl)-4,5-methylenedioxy]-2-naphthalenecarboxoyl}piperazide; N-{6-[3-(1-adamantyl)-4,5-methylenedioxy]-2-naphthalenecarboxoyl}homopiperazide; N-(2-aminoethyl)-{6-[3-(1-adamantyl)-4,5-methylenedioxyphenyl]-2-naphthalenecarboxamide}; and 6-[3-(3-methyl-1-adamantyl)-4-hydroxyphenyl]-2-naphthalenecarboxylic acid.

12. The method of claim 1, wherein said method comprises administration of a compound selected from the group consisting of 6-[3-(1-adamantyl)-4-methoxyphenyl]-2-naphthoic acid; 2-[3-(1-adamantyl)-4-methoxyphenyl]-5-benzimidazole carboxylic acid; 6-[3-(1-adamantyl)-4-hydroxymethylphenyl]-2-naphthoic acid; 6-[3-(1-adamantyl)-4-hydroxy-5-methoxyphenyl]-2-naphthoic acid; 6-[3-(1-adamantyl)-4-acetoxymethylphenyl]-2-naphthoic acid; and 6-[3-(1-adamantyl)-4,5-methylenedioxyphenyl]-2-naphthoic acid.

13. The method of claim 1, wherein the compound is of formula (V) set forth below:

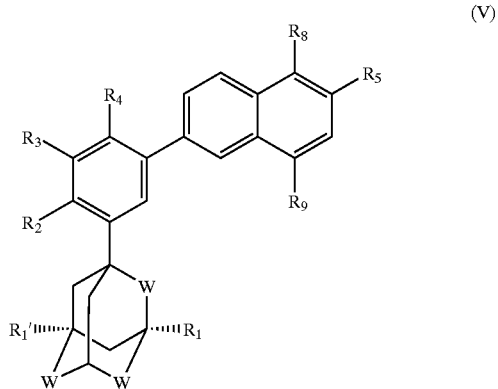

or comprises a pharmaceutically acceptable salt, or geometric and/or optical isomer thereof, with the proviso that said compound is not an RAR-γ receptor-specific agonist ligand.

14. The method of claim 13, wherein the compound of formula (V), $R_5$ is a hydroxycarbonyl radical and/or $R_2$ is a hydroxyl radical, an alkoxyl radical or $R_2$ and $R_3$ together form an —O—CH₂—O radical.

15. The method of claim 1, wherein the retinoid compound is administered systemically, enterally, parenterally, topically, or ocularly.

16. The method of claim 15, wherein the therapeutic dosage ranges from 0.01 mg/kg to 100 mg/kg body weight.

17. The method of claim 1, wherein said cancer is a human cervical cancer or precancer.

18. The method of claim 17, wherein said human cervical cancer or precancer is selected from the group consisting of cervical intraepithelial neoplasia (level I, II or III) and cervical carcinoma.

19. The method of claim 17, wherein said compound is selected from the group consisting of 6-[3-(1-adamantyl)-

4-methoxyphenyl]-2-naphthoic acid; 2-[3-(1-adamantyl)-4-methoxyphenyl]-5-benzimidazole carboxylic acid; 6-[3-(4-adamantyl)-4-hydroxymethylphenyl]-2-naphthoic acid; 6-[3-(1-adamantyl)-4-hydroxy-5-methoxyphenyl]-2-naphthoic acid; 6-[3-(1-adamantyl)-4-acetoxymethylphenyl]-2-naphthoic acid; 6-[3-(1-adamantyl)-4,5-methylenedioxyphenyl]-2-naphthoic acid; N-{6-[3-(1-adamantyl)-4-methoxyphenyl]-2-naphthalenecarboxoyl}piperizide; 4-{3-oxo-3-[3-(1-adamantyl)-4-methoxyphenyl]-1-propynyl}benzoic acid; 4-[N-(3-(1-adamantyl)-4-methoxybenzoyl)amido]2-methoxybenzoic acid; 2-[3-(1-adamantyl)-4-methoxyphenyl]-5-methylbenzimidazole; 6-[3-(1-adamantyl)-4-(1,2-dihydroxyethyl)phenyl]-2-naphthoic acid; 6-[3-(1-adamantyl)-4-hydroxy-6-methylphenyl]-2-naphthoic acid; 6-[3-(1-adamantyl)-4-methoxy-6-methylphenyl]-2-naphthoic acid; 6-[3-(1-adamantyl)-4-hydroxyphenyl]-2-hydroxymethylnaphthalene; 4-[3-(1-adamantyl)-4-methoxybenzyloxy]benzoic acid; 2-[3-(1-adamantyl)-4-methoxyphenyl]-5-benzofurancarboxylic acid; methyl ester of 6-[3-(1-adamantyl)-4-hydroxyphenyl]-2-naphthoic acid; methyl ester of 1-methyl-4-hydroxy-6-[3-(1-adamantyl)-4-methoxyphenyl]-2-naphthoic acid; N-{4-[N-(3-(1-adamantyl)-4-methoxybenzoyl)amido]benzoyl}morpholide; 4-[3-(1-adamantyl)-4-methoxybenzoyloxy]-2-fluorobenzoic acid; 4-hydroxycarbonyl-2-fluorophenyl ester of 3-(1-adamantyl-4-methoxybenzoic acid; 6-[3-(1-adamantyl)-4-ethylphenyl]-2-naphthoic acid; 6-[3-(1-adamantyl)-4-(3-hydroxypropoxy)phenyl]-2-naphthoic acid; 6-[3-(1-adamantyl)-4-aminocarbonylphenyl]-2-naphthoic acid; N-(4-carboxyphenyl)-3-(1-adamantyl)-3-oxopropionamide; 2-hydroxy-4-{2-[3-(1-adamantyl)-4-methoxyphenyl]-2-hydroxyethoxy}benzoic acid; (S)-6-[3-(1-adamantyl)-4-(2S,3-dihydroxypropoxy)phenyl]-2-naphthoic acid; (E) 4-{3-oxo-3-[3-methoxy-4-(1-adamantyl)phenyl]prop-1-enyl}benzoic acid; (E) 4-{3-oxo-3-[4-(2-methoxyethoxymethoxy)-3-(1-adamantyl)phenyl]prop-1-enyl}benzoic acid; (E) 4-{2-[4-(6-aminocarbonylpentyloxy)-3-(1-adamantyl)phenyl]ethenyl}benzoic acid; 3-(1-adamantyl)-4-methoxy-N-(4-carboxyphenyl)benzamidine; 4"-Erythromycin A ester of 6-[3-(1-adamantyl)-4-methoxyphenyl]2-naphthoic acid; 4-carboxyphenyl ester of 3-(1-adamantyl)-4-(2,3-dihydroxyproxy)benzoic acid; 6-[3-(1-adamantyl)-4-(2,3-dihydroxypropoxy)phenyl]-2-naphthoic acid; N-4-carboxyphenyl 3-(1-adamantyl)-4-(methoxycarbonyl) benzamide; 6-[3-(1-adamantyl)-4,5-dihydroxyphenyl]-2-naphthoic acid; 6-[3-(3-methyl-1-adamantyl)-4,5-methylenedioxyphenyl]-2-naphthoic acid; 6-[3-(2-oxa-1-adamantyl)-4,5-methylenedioxyphenyl]-2-naphthoic acid; 6-[3-(2-oxa-1-adamantyl)-4-methoxyphenyl]-2-naphthoic acid; 6-[3-(2-oxa-3-methyl-1-adamantyl)-4-methoxyphenyl]-2-naphthoic acid; 6-[3-(3-methyl-1-adamantyl)-4-methoxyphenyl]-2-naphthoic acid; 6-[3-(3,5-dimethyl-1-adamantyl)-4-methoxyphenyl]-2-naphthoic acid; 6-[3-(3,5-dimethyl-1-adamantyl)-4,5-methylenedioxyphenyl]-2-naphthoic acid; N-{6-[3-(1-adamantyl)-4-methoxyphenyl]-2-naphthalenecarboxoyl}homopiperazide; N-(2-aminoethyl)-{6-[3-(1-adamantyl)-4-methoxyphenyl]-2-naphthalenecarboxamide]; N-{6-[3-(1-adamantyl)-4,5-methylenedioxy-2-naphthalenecarboxoyl}piperazide; N-{6-[3-(1-adamantyl)-4,5-methylenedioxy]-2-naphthalenecarboxoyl}homopiperazide; N-(2-aminoethyl)-{6-[3-(1-adamantyl)-4,5-methylenedioxyphenyl]-2-naphthalenecarboxamide}; and 6-[3-(3-methyl-1-adamantyl)-4-hydroxyphenyl]-2-naphthalenecarboxylic acid.

20. The method of claim 18, wherein said compound is selected from the group consisting of 6-[3-(1-adamantyl)-4-methoxyphenyl]-2-naphthoic acid; 2-[3-(1-adamantyl)-4-methoxyphenyl]-5-benzimidazole carboxylic acid; 6-[3-(1-adamantyl)-4-hydroxymethylphenyl]-2-naphthoic acid; 6-[3-(1-adamantyl)-4-hydroxy-5-methoxyphenyl]-2-naphthoic acid; 6-[3-(1-adamantyl)-4-acetoxymethylphenyl]-2-naphthoic acid; 6-[3-(1-adamantyl)-4,5-methylenedioxyphenyl]-2-naphthoic acid; N-{6-[3-(1-adamantyl)-4-methoxyphenyl]-2-naphthalenecarboxoyl}piperizide; 4-{3-oxo-3-[3-(1-adamantyl)-4-methoxyphenyl]-1-propynyl}benzoic acid; 4-[N-(3-(1-adamantyl)-4-methoxybenzoyl)amido]2-methoxybenzoic acid; 2-[3-(1-adamantyl)-4-methoxyphenyl]-5-methylbenzimidazole; 6-[3-(1-adamantyl)-4-(1,2-dihydroxyethyl)phenyl]-2-naphthoic acid; 6-[3-(1-adamantyl)-4-hydroxy-6-methylphenyl]-2-naphthoic acid; 6-[3-(1-adamantyl)-4-methoxy-6-methylphenyl]-2-naphthoic acid; 6-[3-(1-adamantyl)-4-hydroxyphenyl]-2-hydroxymethylnaphthalene; 4-[3-(1-adamantyl)-4-methoxybenzyloxy]benzoic acid; 2-[3-(1-adamantyl)-4-methoxyphenyl]-5-benzofurancarboxylic acid; methyl ester of 6-[3-(1-adamantyl)-4-hydroxyphenyl]-2-naphthoic acid; methyl ester of 1-methyl-4-hydroxy-6-[3-(1-adamantyl)-4-methoxyphenyl]-2-naphthoic acid; N-{4-[N-(3-(1-adamantyl)-4-methoxybenzoyl)amido]benzoyl}morpholide; 4-[3-(1-adamantyl)-4-methoxybenzoyloxy]-2-fluorobenzoic acid; 4-hydroxycarbonyl-2-fluorophenyl ester of 3-(1-adamantyl-4-methoxybenzoic acid; 6-[3-(1-adamantyl)-4-ethylphenyl]-2-naphthoic acid; 6-[3-(1-adamantyl)-4-(3-hydroxypropoxy)phenyl]-2-naphthoicacid; 6-[3-(1-adamantyl)-4-aminocarbonylphenyl]-2-naphthoic acid; N-(4-carboxyphenyl)-3-(1-adamantyl)-3-oxopropionamide; 2-hydroxy-4-{2-[3-(1-adamantyl)-4-methoxyphenyl]-2-hydroxyethoxy}benzoic acid; (S)-6-[3-(1-adamantyl)-4-(2S,3-dihydroxypropoxy)phenyl]-2-naphthoic acid; (E) 4-{3-oxo-3-[3-methoxy-4-(1-adamantyl)phenyl]prop-1-enyl}benzoic acid; (E) 4-{3-oxo-3-[4-(2-methoxyethoxymethoxy)-3-(1-adamantyl)phenyl]prop-1-enyl}benzoic acid; (E) 4-{2-[4-(6-aminocarbonylpentyloxy)-3-(1-adamantyl)phenyl]ethenyl}benzoic acid; 3-(1-adamantyl)-4-methoxy-N-(4-carboxyphenyl)benzamidine; 4"-Erythromycin A ester of 6-[3-(1-adamantyl)-4-methoxyphenyl]2-naphthoic acid; 4-carboxyphenyl ester of 3-(1-adamantyl)-4-(2,3-dihydroxyproxy)benzoic acid; 6-[3-(1-adamantyl)-4-(2,3-dihydroxypropoxy)phenyl]-2-naphthoic acid; N-4-carboxyphenyl 3-(1-adamantyl)-4-(methoxycarbonyl) benzamide; 6-[3-(1-adamantyl)-4,5-dihydroxyphenyl]-2-naphthoic acid; 6-[3-(3-methyl-1-adamantyl)-4,5-methylenedioxyphenyl]-2-naphthoic acid; 6-[3-(2-oxa-1-adamantyl)-4,5-methylenedioxyphenyl]-2-naphthoic acid; 6-[3-(2-oxa-1-adamantyl)-4-methoxyphenyl]-2-naphthoic acid; 6-[3-(2-oxa-3-methyl-1-adamantyl)-4-methoxyphenyl]-2-naphthoic acid; 6-[3-(3-methyl-1-adamantyl)-4-methoxyphenyl]-2-naphthoic acid; 6-[3-(3,5-dimethyl-1-adamantyl)-4-methoxyphenyl]-2-naphthoic acid; 6-[3-(3,5-dimethyl-1-adamantyl)-4,5-methylenedioxyphenyl]-2-naphthoic acid; N-{6-[3-(1-adamantyl)-4-methoxyphenyl]-2-naphthalenecarboxoyl}homopiperazide; N-(2-aminoethyl)-{6-[3-(1-adamantyl)-4-methoxyphenyl]-2-naphthalenecarboxamide]; N-{6-[3-(1-adamantyl)-4,5-methylenedioxy]-2-naphthalenecarboxoyl}piperazide; N-{6-[3-(1-adamantyl)-4,5-methylenedioxy]-2-naphthalenecarboxoyl}homopiperazide; N-(2-aminoethyl)-

{6-[3-(1-adamantyl)-4,5-methylenedioxyphenyl]-2-naphthalenecarboxamide}; and 6-[3-(3-methyl-1-adamantyl)-4-hydroxyphenyl]-2-naphthalenecarboxylic acid.

21. The method of claim 19, wherein said compound is selected from the group consisting of 6-[3-(1-adamantyl)-4-methoxyphenyl]-2-naphthoic acid, 2-[3-(1-adamantyl)-4-methoxyphenyl]-5-benzimidazole carboxylic acid, 6-[3-(1-adamantyl)-4,5-methylenedioxyphenyl]-2-naphthoic acid, and mixtures thereof.

22. The method of claim 20, wherein said compound is selected from the group consisting of 6-[3-(1-adamantyl)-4-methoxyphenyl]-2-naphthoic acid, 2-[3-(1-adamantyl)-4-methoxyphenyl]-5-benzimidazole carboxylic acid, 6-[3-(1-adamantyl)-4,5-methylenedioxyphenyl]-2-naphthoic acid, and mixtures thereof.

23. The method of claim 17, wherein said compound is administered systemically, enterally, parenterally, topically or ocularly.

24. The method of claim 18, wherein said compound is administered systemically, enterally, parenterally, topically or ocularly.

25. The method of claim 19, wherein said compound is administered systemically, enterally, parenterally, topically or ocularly.

26. The method of claim 20, wherein said compound is administered systemically, enterally, parenterally, topically or ocularly.

27. The method of claim 21, wherein said compound is administered systemically, enterally, parenterally, topically or ocularly.

28. The method of claim 22, wherein said compound is administered systemically, enterally, parenterally, topically or ocularly.

29. The method of claim 17, wherein the effective dosage ranges from 0.01 mg/kg to 100 mg/kg body weight.

30. The method of claim 18, wherein the effective dosage ranges from 0.01 mg/kg to 100 mg/kg body weight.

31. The method of claim 19, wherein the effective dosage ranges from 0.01 mg/kg to 100 mg/kg body weight.

32. The method of claim 20, wherein the effective dosage ranges from 0.01 mg/kg to 100 mg/kg body weight.

33. The method of claim 21, wherein the effective dosage ranges from 0.01 mg/kg to 100 mg/kg body weight.

34. The method of claim 22, wherein the effective dosage ranges from 0.01 mg/kg to 100 mg/kg body weight.

35. The method of claim 17, wherein a gel-containing said compound is applied to the cervix of a patient in need of such treatment.

36. The method of claim 35, wherein said compound is applied by use of a cervical cap and a collagen sponge.

37. The method of claim 35, wherein the compound is selected from the group consisting of 6-[3-(1-adamantyl)-4-methoxyphenyl]-2-naphthoic acid, 2-[3-(1-adamantyl)-4-methoxyphenyl]-5-benzimidazole carboxylic acid, 6-[3-(1-adamantyl)-4,5-methylenedioxyphenyl]-2-naphthoic acid, and mixtures thereof.

38. The method of claim 36, wherein the compound is selected from the group consisting of 6-[3-(1-adamantyl)-4-methoxyphenyl]-2-naphthoic acid, 2-[3-(1-adamantyl)-4-methoxyphenyl]-5-benzimidazole carboxylic acid, 6-[3-(1-adamantyl)-4,5-methylenedioxyphenyl]-2-naphthoic acid, and mixtures thereof.

39. The method of claim 17, wherein the cancer or precancer is cervical intraepithelial neoplasia, and the compound is 6-[3-(1-adamantyl)-4-methoxyphenyl]-2-napthoic acid.

40. An aqueous gel formulation suitable for treatment and/or prevention of cervical cancer or precancer containing a therapeutically effective amount of at least one compound selected from the group consisting of 6-[3-(1-adamantyl)-4-methoxyphenyl]-2-naphthoic acid, 2-[3-(1-adamantyl)-4-methoxyphenyl]-5-benzimidazole carboxylic acid, 6-[3-(1-adamantyl)-4,5-methylenedioxyphenyl]-2-naphthoic acid, and mixtures thereof, and a pharmaceutically acceptable carrier, which is topically applicable in combination with a cervical cap and a collagen sponge.

41. A composition adopted for the prevention and/or treatment of cervical cancer or precancer that comprises a prophylactically or therapeutically effective amount of at least one compound selected from the group consisting of 6-[3-(1-adamantyl)-4-methoxyphenyl]-2-naphthoic acid, 2-[3-(1-adamantyl)-4-methoxyphenyl]-5-benzimidazole carboxylic acid, 6-[3-(1-adamantyl)-4,5-methylenedioxyphenyl]-2-naphthoic acid, and mixtures thereof, and a pharmaceutically acceptable carrier.

42. The composition of claim 41, which further comprises at least one other compound selected from another retinoid compound, a D vitamin or derivative thereof, a corticosteroid, an anti-free radical agent, an α-hydroxy or α-keto acid or derivative thereof or an ion channel blocker.

* * * * *